(12) United States Patent
Schmidt et al.

(10) Patent No.: US 6,293,279 B1
(45) Date of Patent: Sep. 25, 2001

(54) AEROSOL MEDICATION DELIVERY APPARATUS AND SYSTEM

(75) Inventors: James N. Schmidt, London (CA); Jerry Grychowski, Lake Zurich, IL (US); Daniel K. Engelbreth, London (CA); Robert Morton, London (CA); Martin P. Foley, London (CA)

(73) Assignee: Trudell Medical International, London (CA)

( * ) Notice: Subject to any disclaimer, the term of this patent is extended or adjusted under 35 U.S.C. 154(b) by 0 days.

(21) Appl. No.: 09/287,997

(22) Filed: Apr. 7, 1999

Related U.S. Application Data

(63) Continuation-in-part of application No. 08/938,686, filed on Sep. 26, 1997.

(51) Int. Cl.[7] .................................................. A61M 11/00
(52) U.S. Cl. ................................ 128/200.23; 128/200.18
(58) Field of Search ....................... 128/200.23, 200.18, 128/200.24, 203.21, 203.18, 203.23, 205.24

(56) References Cited

U.S. PATENT DOCUMENTS

| | | |
|---|---|---|
| 2,670,739 | 3/1954 | McNeill . |
| 3,236,458 | 2/1966 | Ramis . |
| 3,556,122 | * 1/1971 | Laerdal ................................ 137/102 |

(List continued on next page.)

FOREIGN PATENT DOCUMENTS

| | | |
|---|---|---|
| 0 009 667 A1 | 9/1978 | (EP) . |
| 0 015 247 | 1/1980 | (EP) . |
| 0 134 847 | 8/1983 | (EP) . |
| 0 289 563 B1 | 5/1991 | (EP) . |
| 0 514 085 A1 | 5/1991 | (EP) . |
| 0 347 779 B1 | 5/1994 | (EP) . |
| 0 475 257 B1 | 6/1994 | (EP) . |
| 0 548 152 B1 | 7/1996 | (EP) . |
| 0 514 085 B1 | 7/1997 | (EP) . |
| 0 820 780 A1 | 1/1998 | (EP) . |
| 0 585 379 B1 | 9/1998 | (EP) . |
| 975754 | 5/1961 | (GB) . |
| 1 017 032 X | 12/1963 | (GB) . |
| 2 000 555 | 1/1979 | (GB) . |
| 2 299 512 A | 10/1996 | (GB) . |

(List continued on next page.)

OTHER PUBLICATIONS

Merriam–Webster's Collegiate Dictionary, Tenth Ed., p. 86, ISBN 0–87779–707–2.
Callahan, "K981944–BreatheRite," letter from Dept. of Health & Human Services, with enclosure, 8/98.
Ventlab Corporation, "Ventlab BreatheRite," Web page from http://www.ventlab.com/mdi.htm, Dec. 15, 2000.

(List continued on next page.)

*Primary Examiner*—John G. Weiss
*Assistant Examiner*—Teena Mitchell
(74) *Attorney, Agent, or Firm*—Brinks Hofer Gilson & Lione

(57) ABSTRACT

The invention provides an aerosol medication delivery apparatus for use with a pMDI canister having medication and a propellant contained therein under pressure, wherein the pMDI canister has a discharge orifice from which the medication and propellant can be discharged forming an aerosol. The apparatus has a chamber housing having an input end and an output end and defining an interior space, wherein the input end receives the medication discharged from the discharge orifice of the pMDI canister into the interior space and wherein the medication can be withdrawn from the interior space by inhalation by a patient from the output end. The aerosol medication delivery apparatus also includes a valve at the output end. The valve has a valve seat and a valve member. The valve seat has a sealing surface and the valve member has a central open area and a sealing portion at the perimeter of the open area that mates with the sealing surface when the valve is closed. The valve allows medication to be withdrawn through the central open area but prevents backflow into the chamber housing.

27 Claims, 18 Drawing Sheets

U.S. PATENT DOCUMENTS

| | | |
|---|---|---|
| 3,565,071 | 2/1971 | Cobb et al. . |
| 3,643,686 * | 2/1972 | Koegel ............................ 128/207.12 |
| 3,809,084 | 5/1974 | Hansen . |
| 3,809,294 | 5/1974 | Torgeson . |
| 3,838,686 | 10/1974 | Szekely . |
| 3,897,779 | 8/1975 | Hansen . |
| 3,994,421 | 11/1976 | Hansen . |
| 4,174,712 | 11/1979 | Moren et al. . |
| 4,292,966 | 10/1981 | Monö et al. . |
| 4,470,412 | 9/1984 | Nowacki et al. . |
| 4,509,515 | 4/1985 | Altounyan et al. . |
| 4,637,528 | 1/1987 | Wachinski et al. . |
| 4,641,644 | 2/1987 | Andersson et al. . |
| 4,796,614 | 1/1989 | Nowacki et al. . |
| 4,846,168 | 7/1989 | Abiko et al. . |
| 4,852,561 | 8/1989 | Sperry . |
| 4,907,583 | 3/1990 | Wetterlin et al. . |
| 4,940,051 | 7/1990 | Lankinen . |
| 5,012,803 | 5/1991 | Foley et al. . |
| 5,012,804 | 5/1991 | Foley et al. . |
| 5,033,463 | 7/1991 | Cocozza . |
| 5,040,527 | 8/1991 | Larson et al. . |
| 5,042,467 | 8/1991 | Foley . |
| 5,048,729 | 9/1991 | Pritchard . |
| 5,178,138 | 1/1993 | Walstrom et al. . |
| 5,241,954 | 9/1993 | Glenn . |
| 5,250,287 | 10/1993 | Cocozza . |
| 5,297,543 | 3/1994 | Larson et al. . |
| 5,385,140 | 1/1995 | Smith . |
| 5,427,089 | 6/1995 | Kraemer . |
| 5,477,849 | 12/1995 | Fry . |
| 5,497,765 * | 3/1996 | Praud et al. .................... 128/200.23 |
| 5,505,194 | 4/1996 | Adjei et al. . |
| 5,617,844 | 4/1997 | King . |
| 5,676,130 | 10/1997 | Gupte et al. . |
| 5,724,959 | 3/1998 | McAughey et al. . |
| 5,724,962 | 3/1998 | Vidgrén et al. . |
| 5,738,087 | 4/1998 | King . |
| 5,755,221 | 5/1998 | Bisgaard . |
| 5,765,553 | 6/1998 | Richards et al. . |
| 5,775,320 | 7/1998 | Patton et al. . |
| 5,816,240 | 10/1998 | Komesaroff . |
| 5,840,279 | 11/1998 | Narodylo et al. . |
| 5,881,718 * | 3/1999 | Mortensen et al. ............. 128/203.11 |
| 6,026,807 | 2/2000 | Puderbaugh et al. . |
| 6,039,042 | 3/2000 | Sladek . |
| 6,123,075 * | 9/2000 | Kirk ................................ 128/205.13 |
| 6,138,673 | 10/2000 | Shepherd . |

FOREIGN PATENT DOCUMENTS

| | | |
|---|---|---|
| WO 91/00117 | 1/1991 | (WO) . |
| WO 96/32149 | 10/1996 | (WO) . |
| WO 97/01365 | 1/1997 | (WO) . |
| WO 97/31668 | 9/1997 | (WO) . |
| WO 98/26827 | 6/1998 | (WO) . |
| WO 99/16490 | 4/1999 | (WO) . |

OTHER PUBLICATIONS

Copies of photographs of Ventlab BreatheRite holding chamber, 12/00.

English language Abstract of EP 820780 A1.

English language Abstract of EP 0 009 667 A1.

Hickey et al., *Aerosol Generation from Propellant–Driven Metered Dose Inhalers*, pp. 417–435, Title and Source unknown.

J.L. Rau, *Respiratory Care Pharmacology*, $4^{th}$ ed. (1994, Mosby), pp. 256–261.

K. Meeran, A. Hattersley, J. Burrin, R. Shiner, K. Ibbertson, Oral and Inhaled Corticosteroids Reduce Bone Formation as Shown by Plasma Osteocalcin Levels, Am. J. Respir. Crit. Care Med 151:333–336.

S.P. Newman, Aerosol Deposition Consideration in Inhalation Therapy, Chest/88/2/Aug., 1985/[Supplement].

* cited by examiner

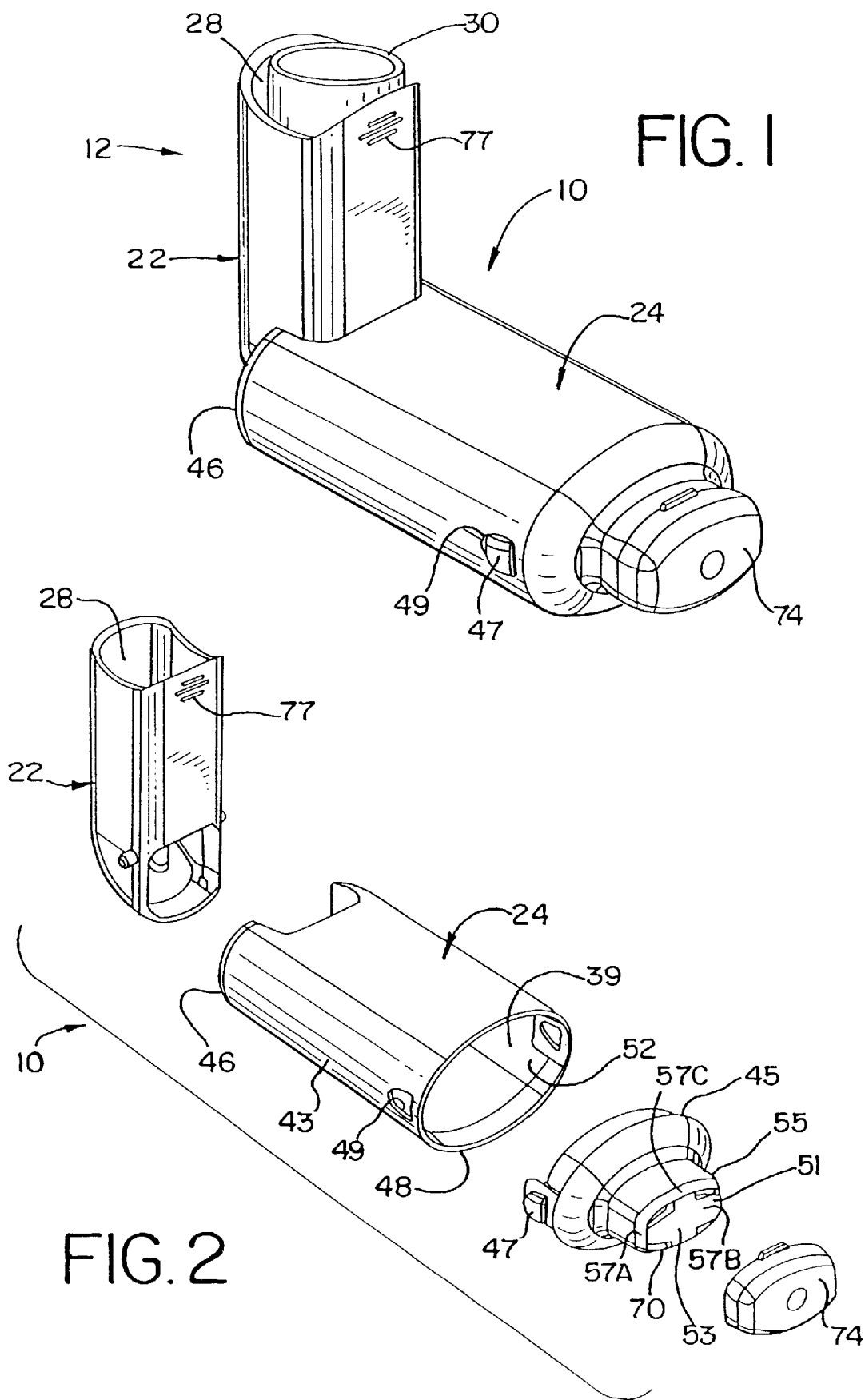

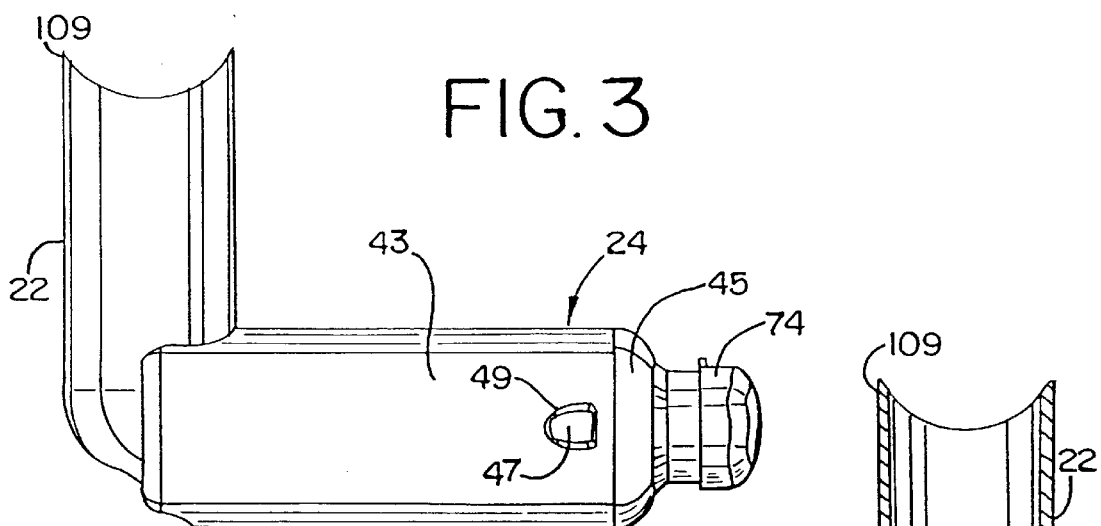
FIG. 3
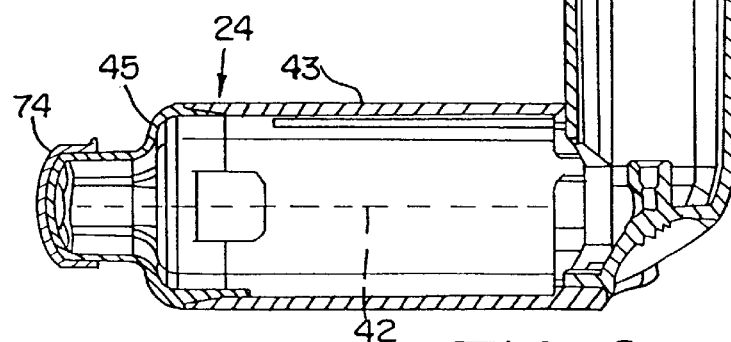
FIG. 4
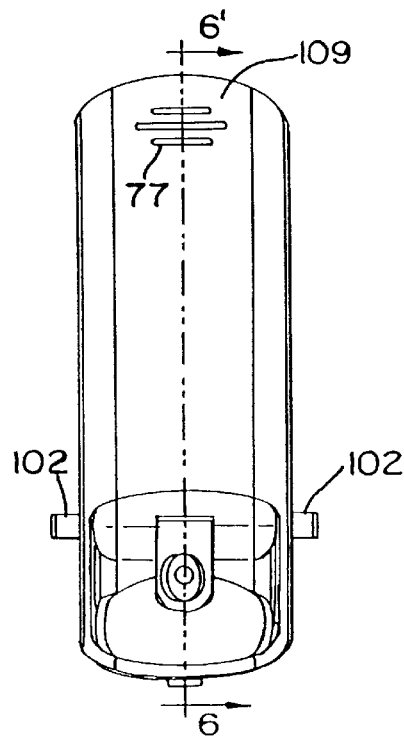
FIG. 5
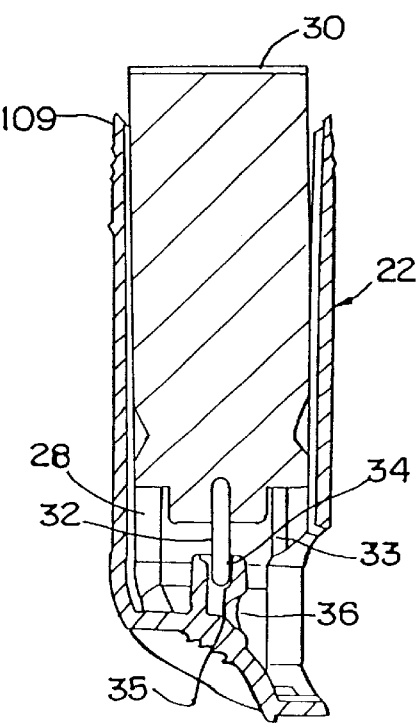
FIG. 6

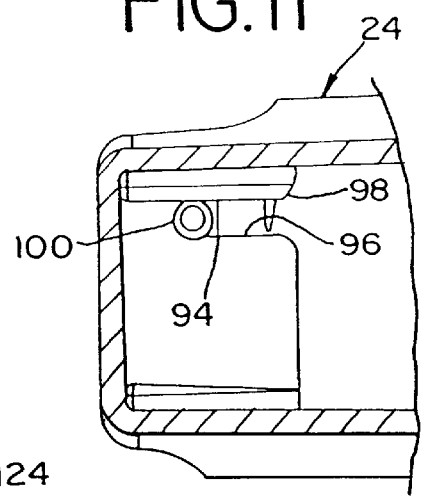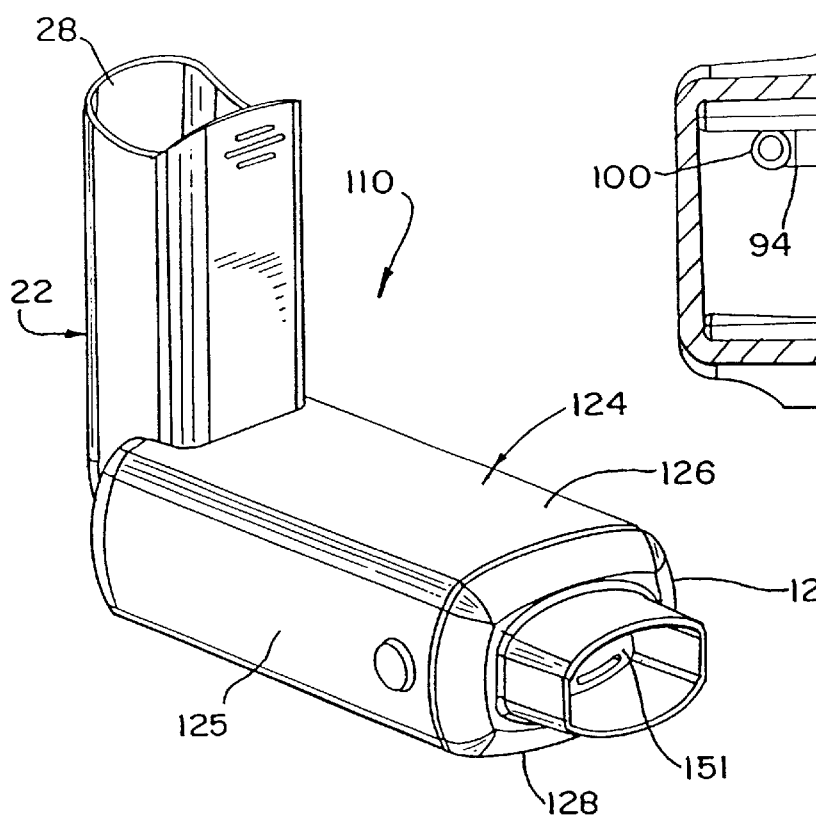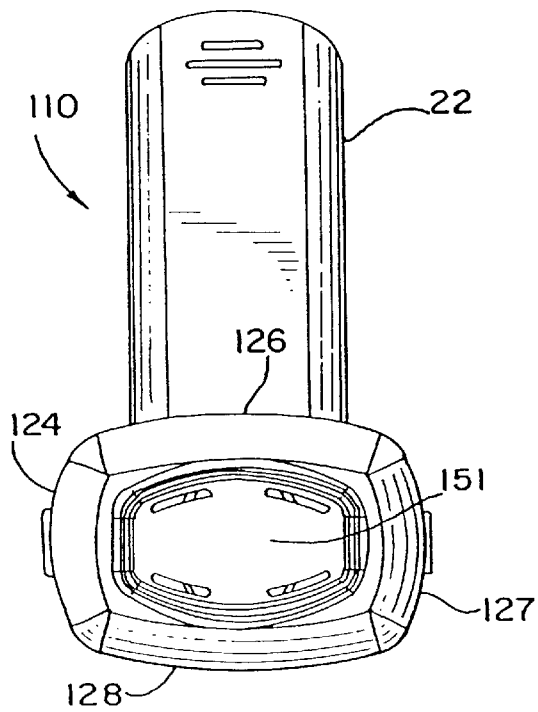

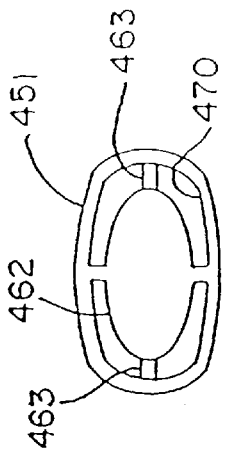
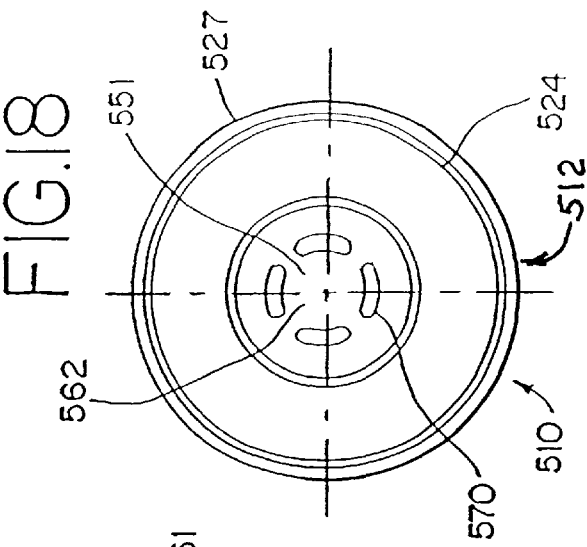
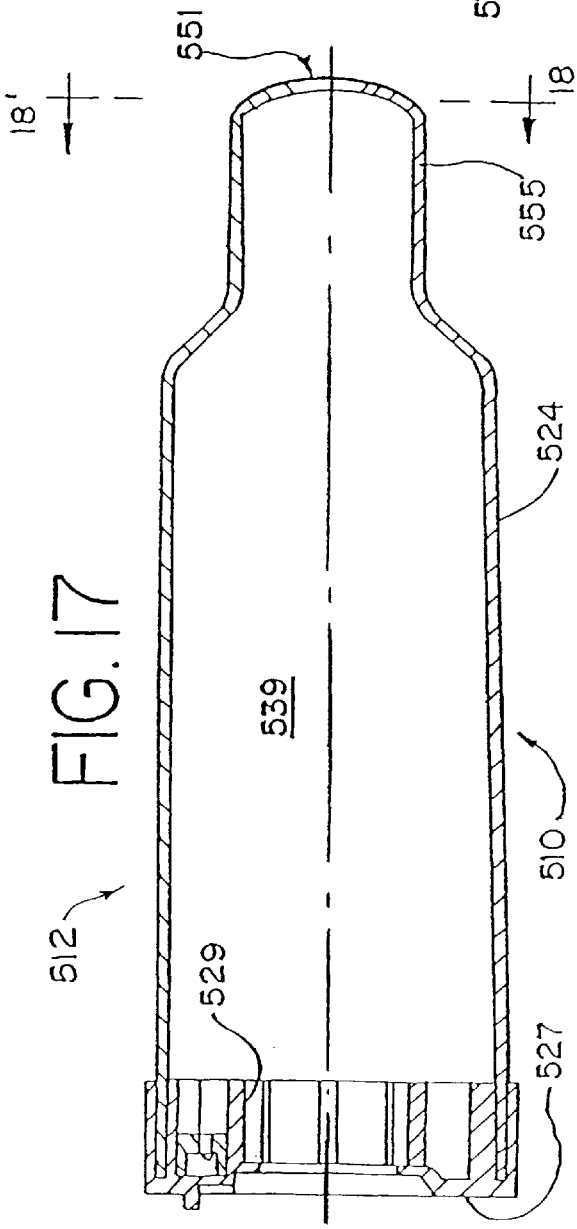

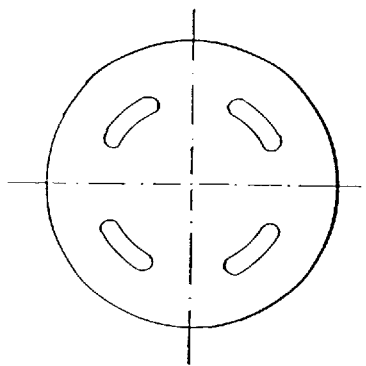
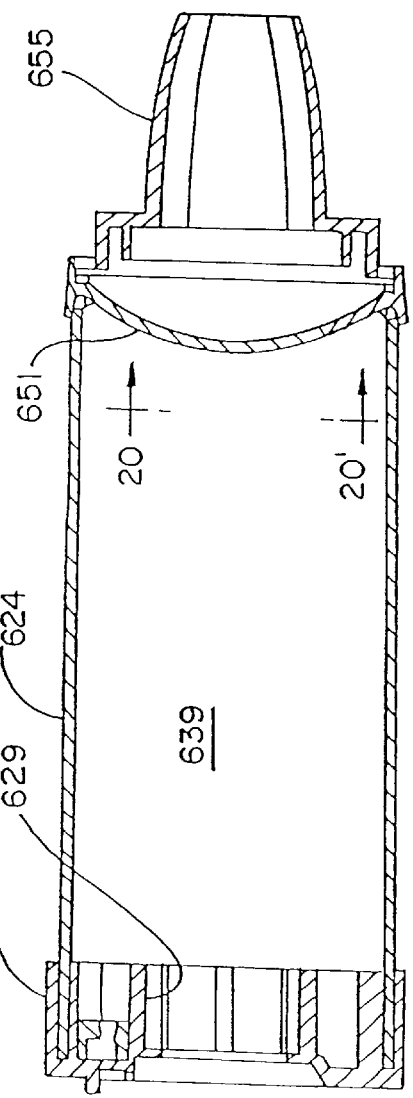
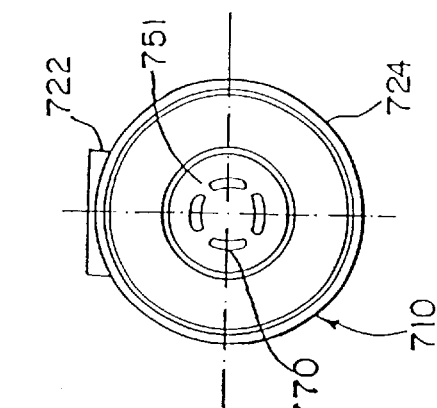
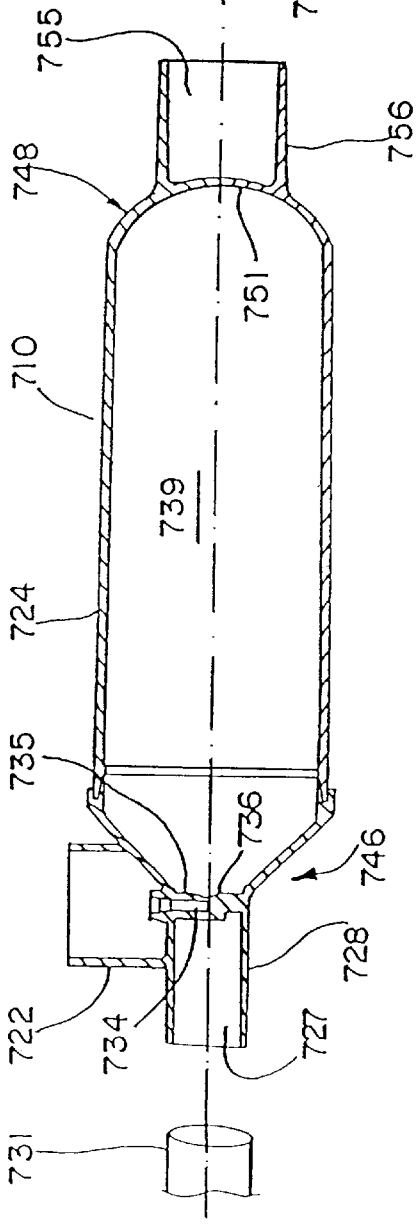

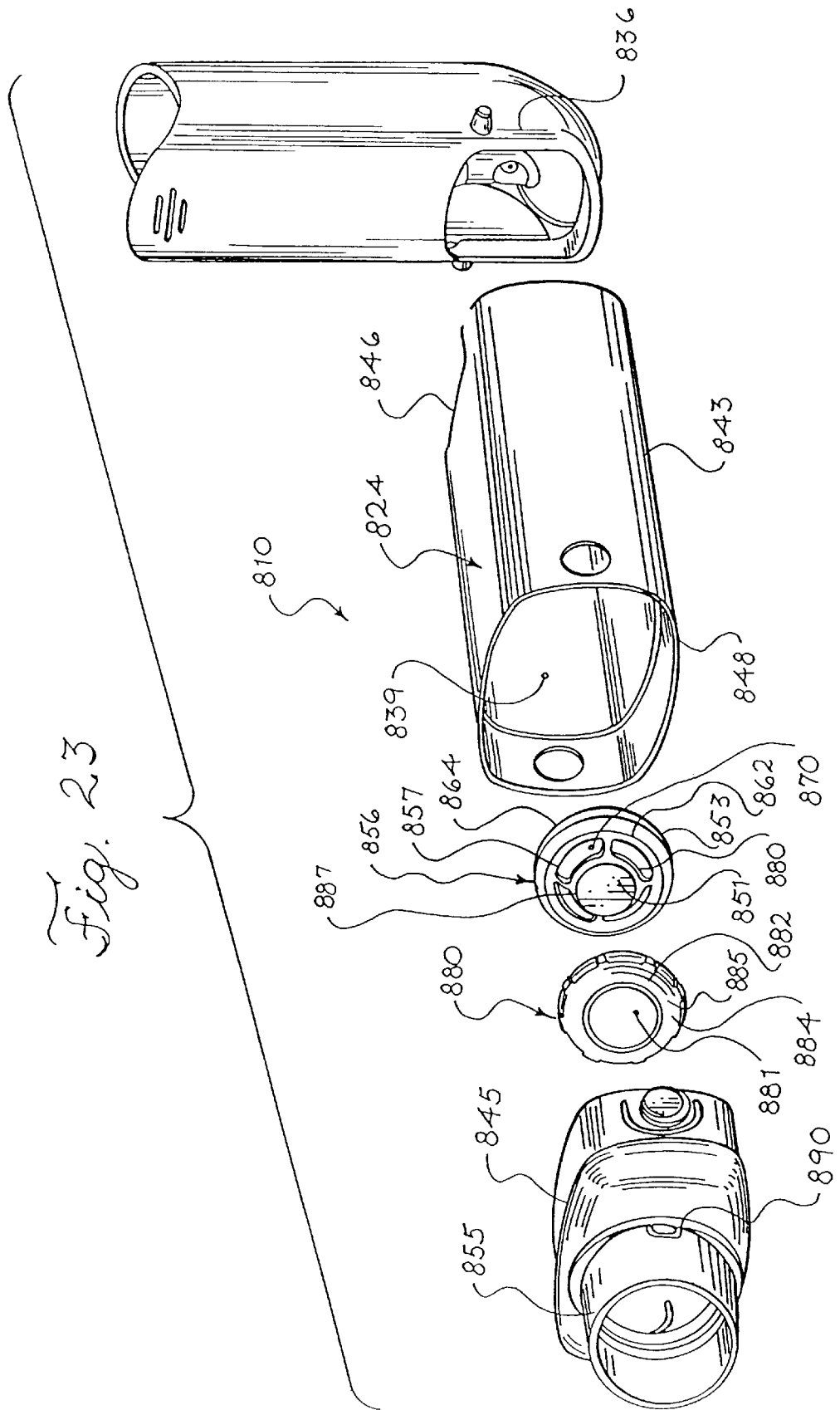

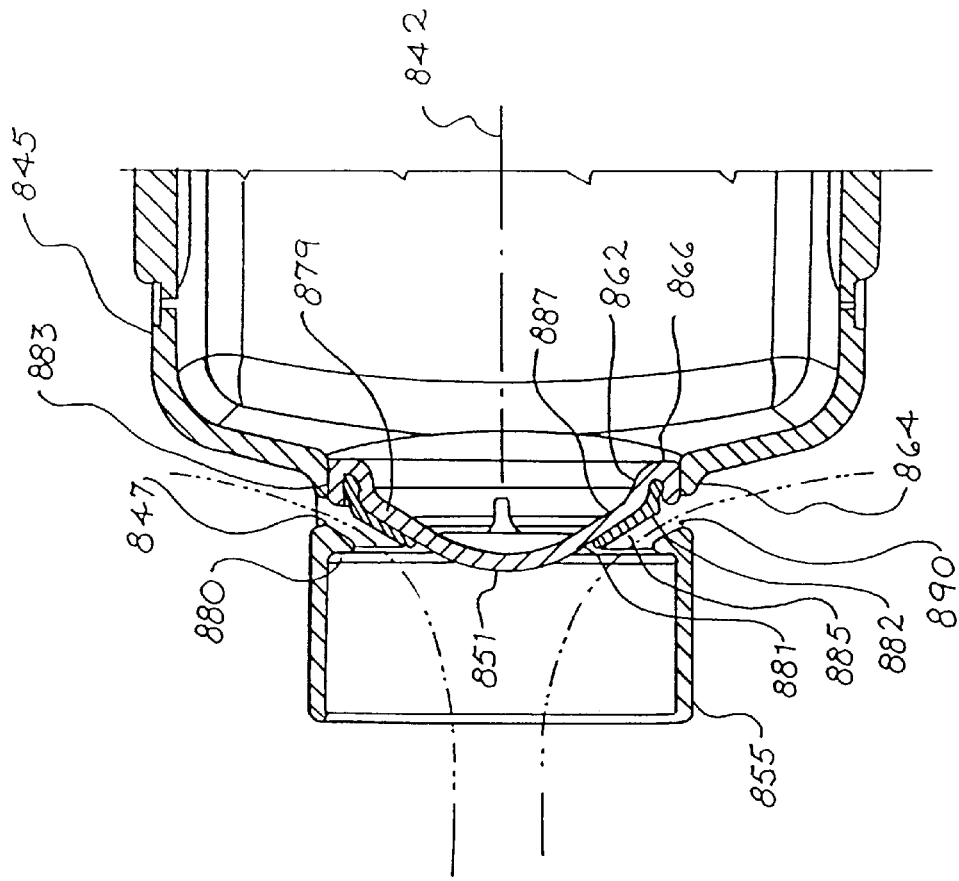
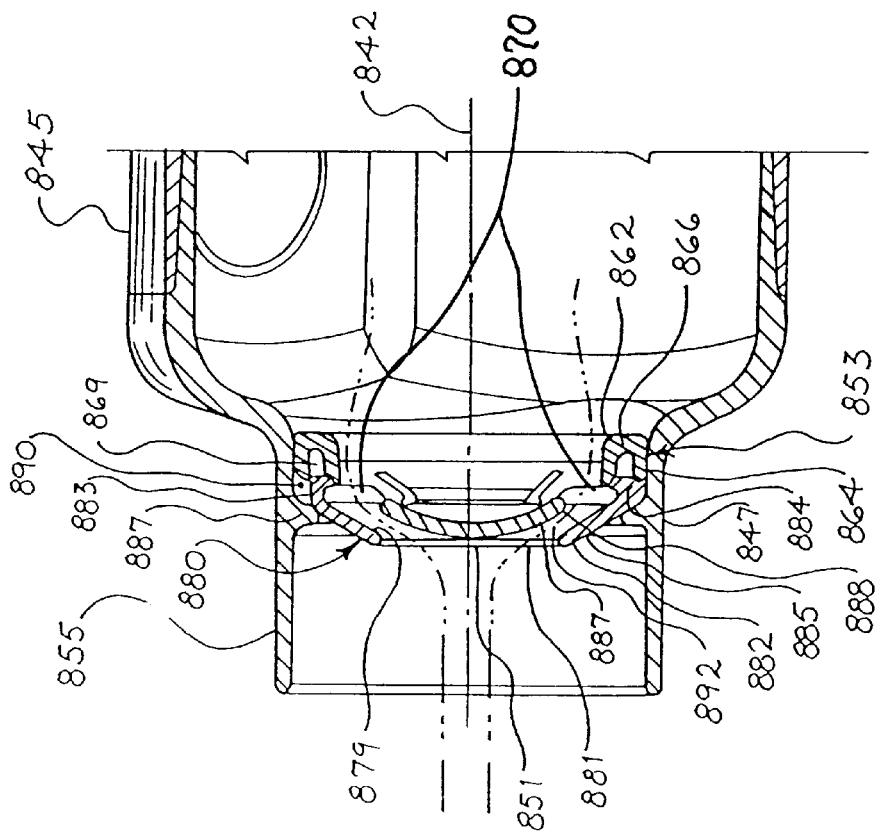

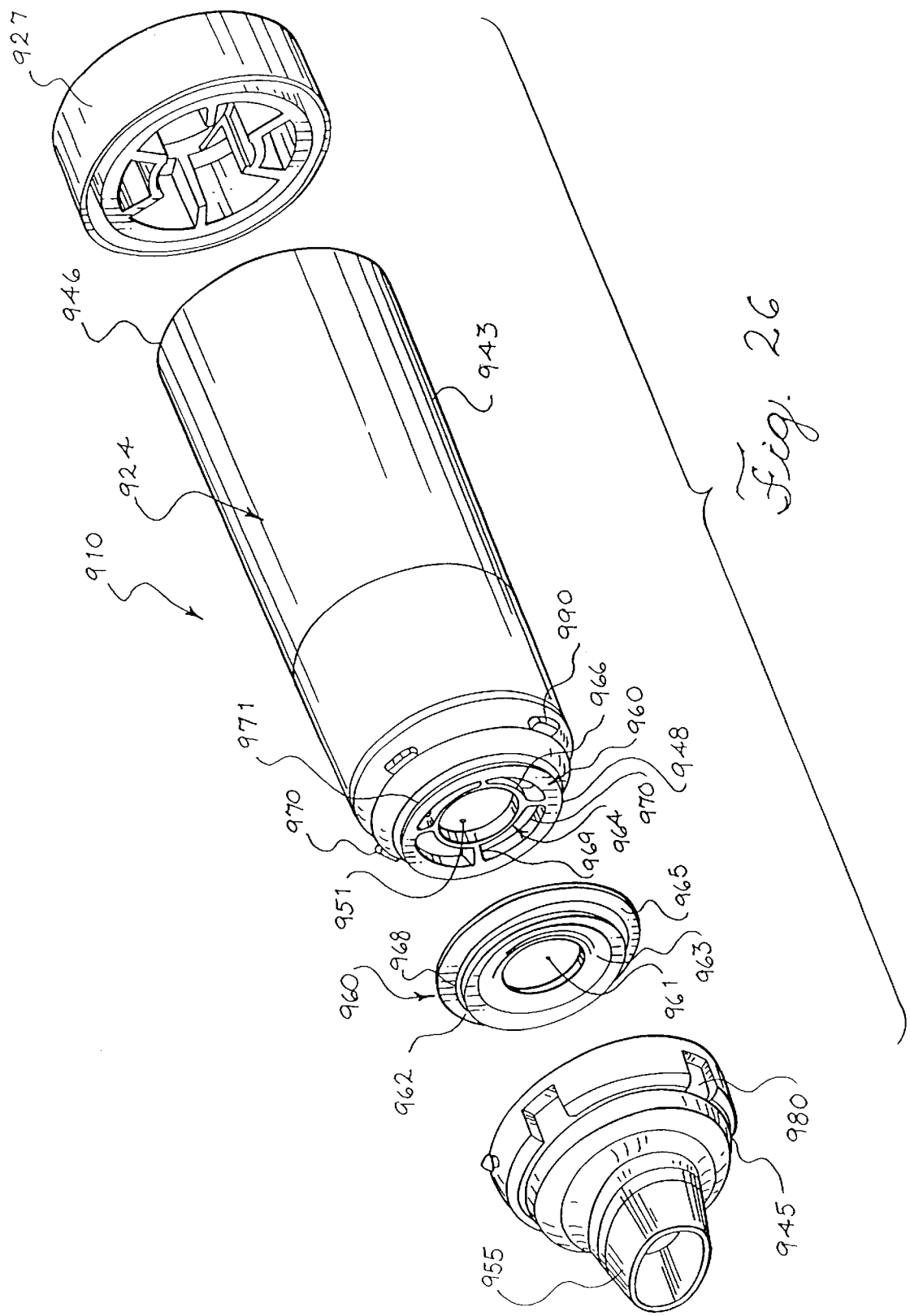

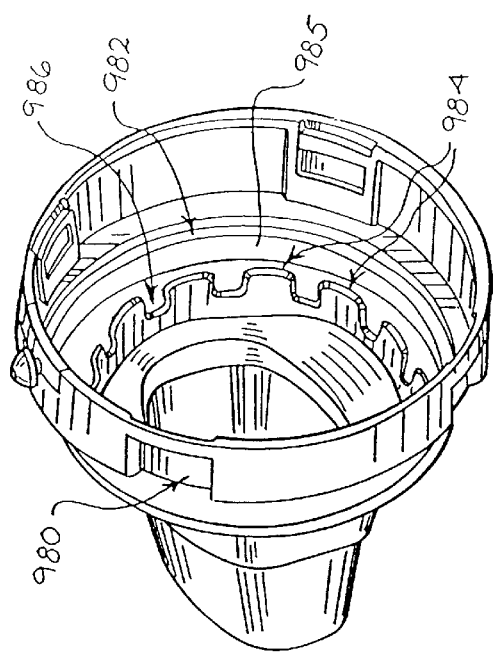
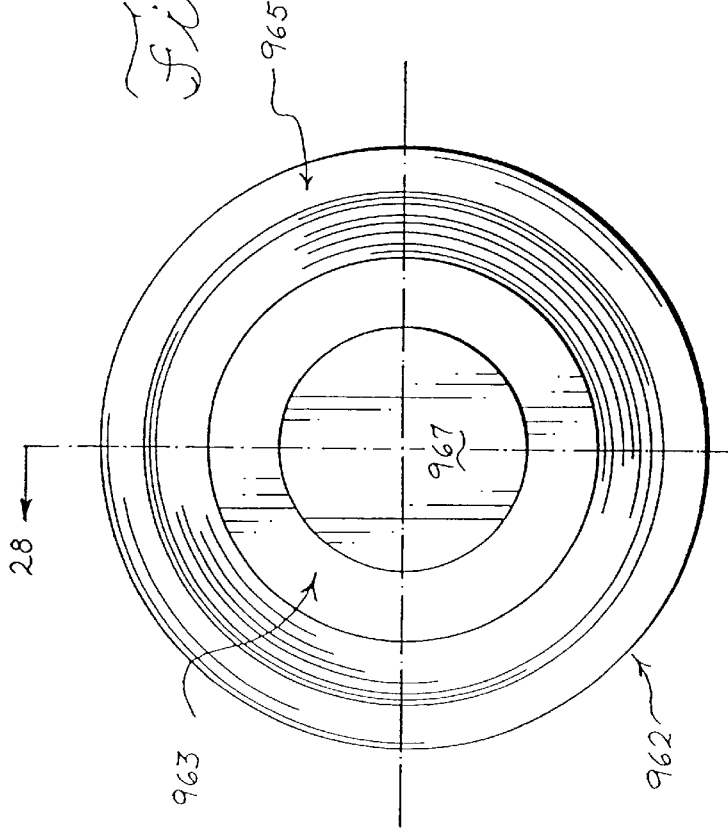
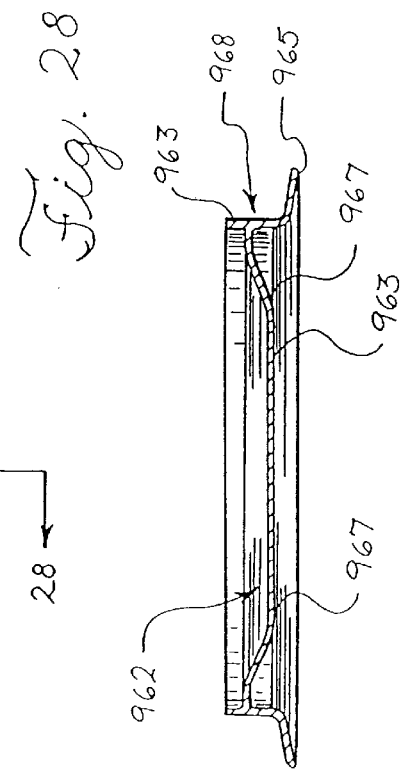

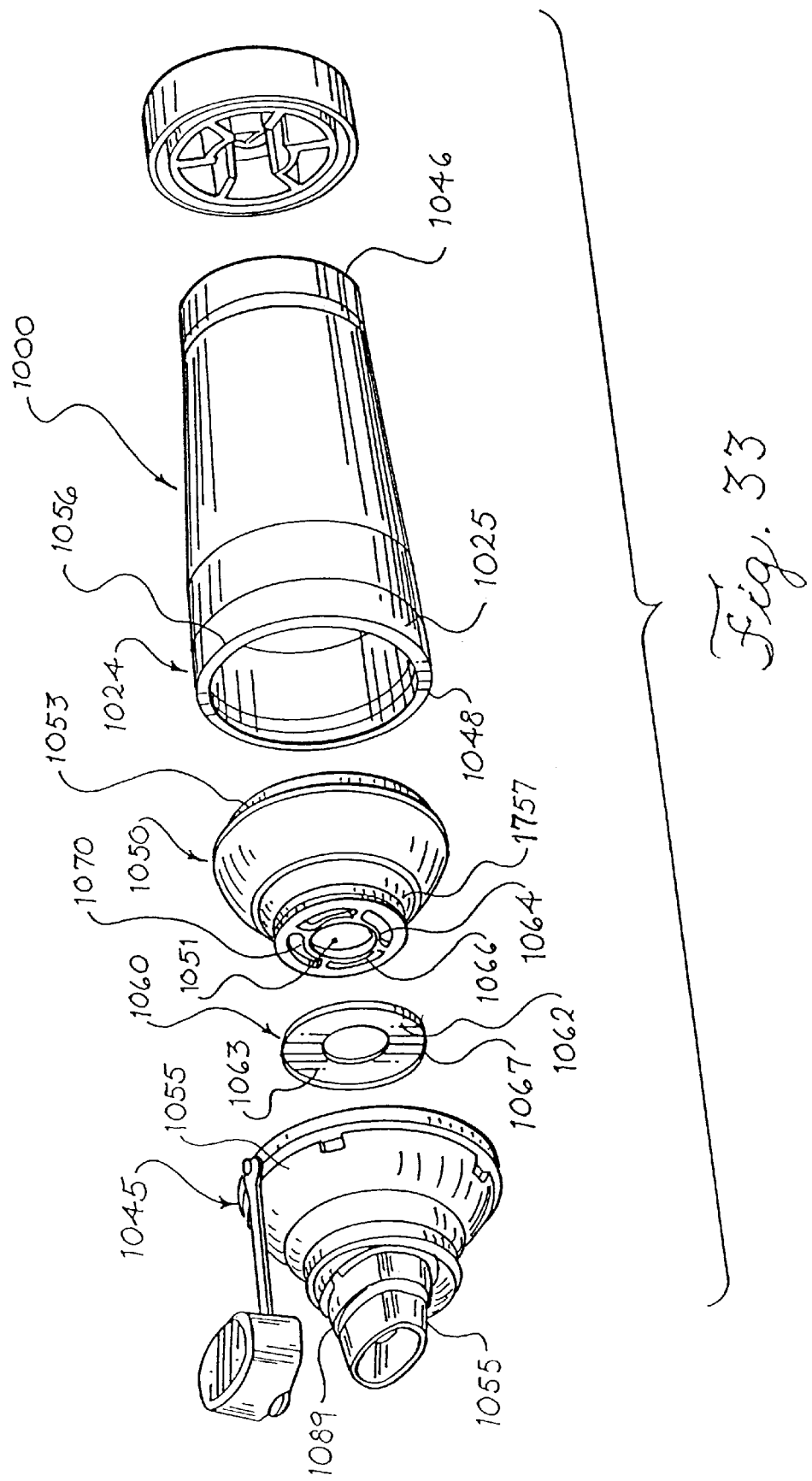

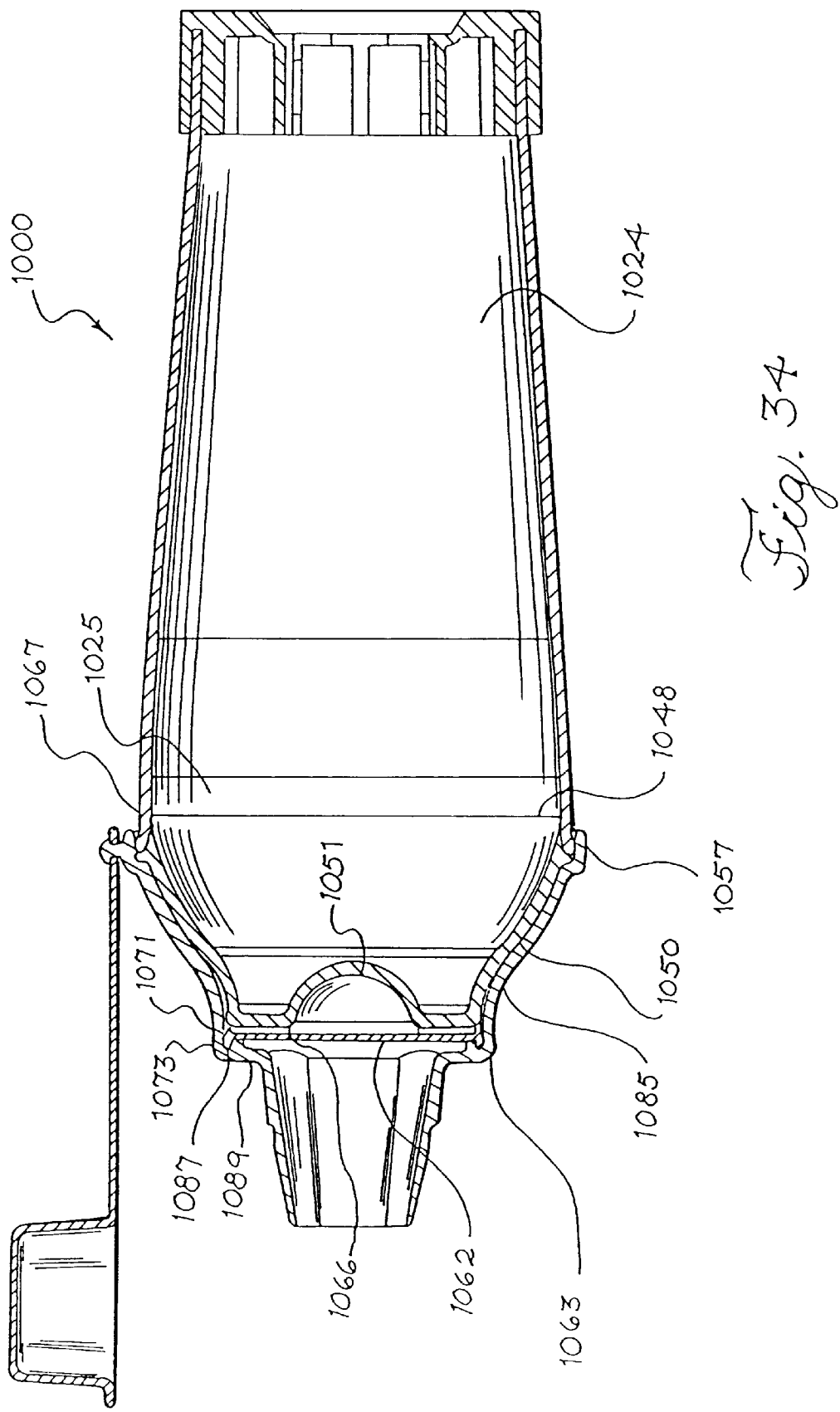

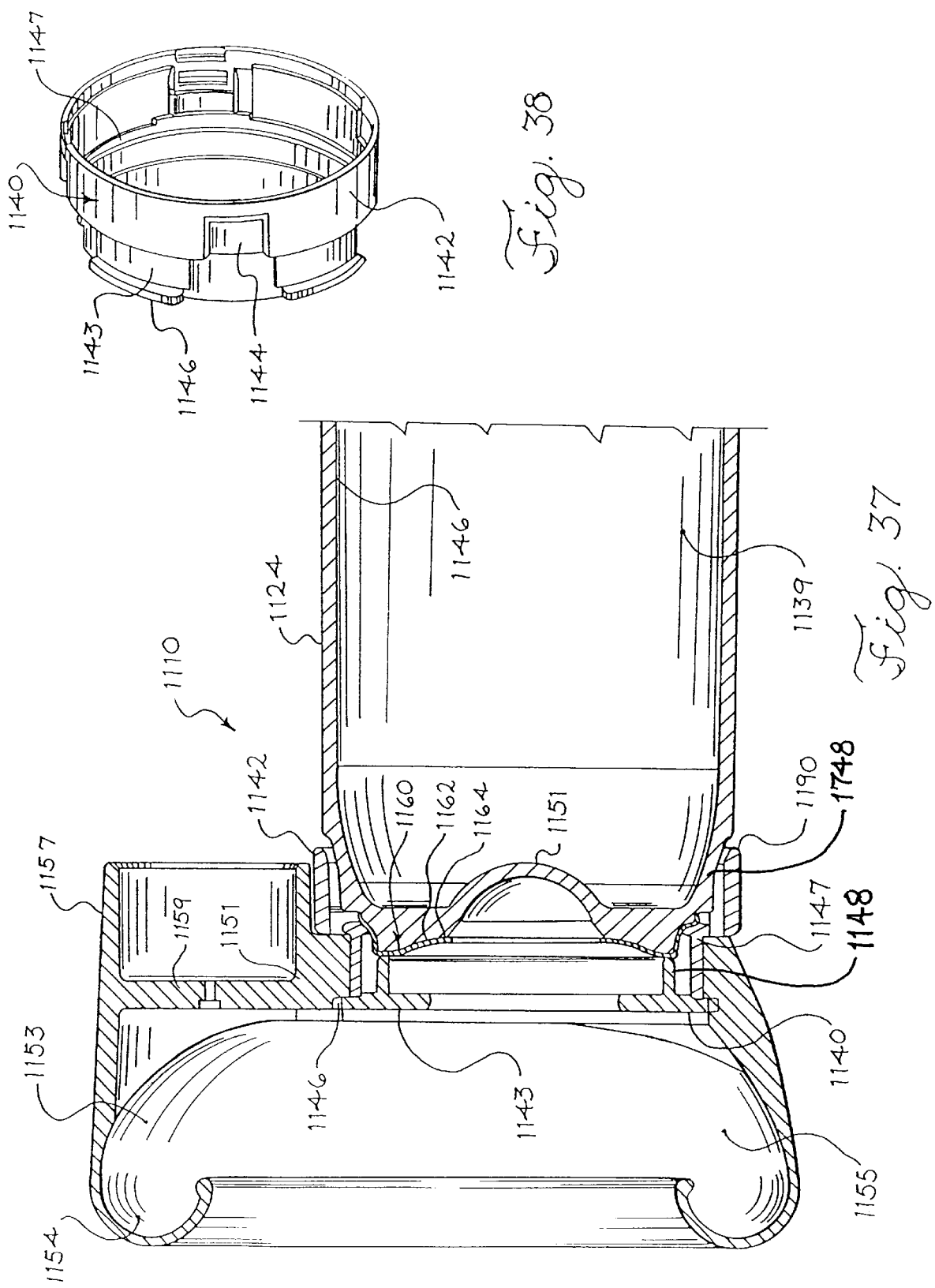

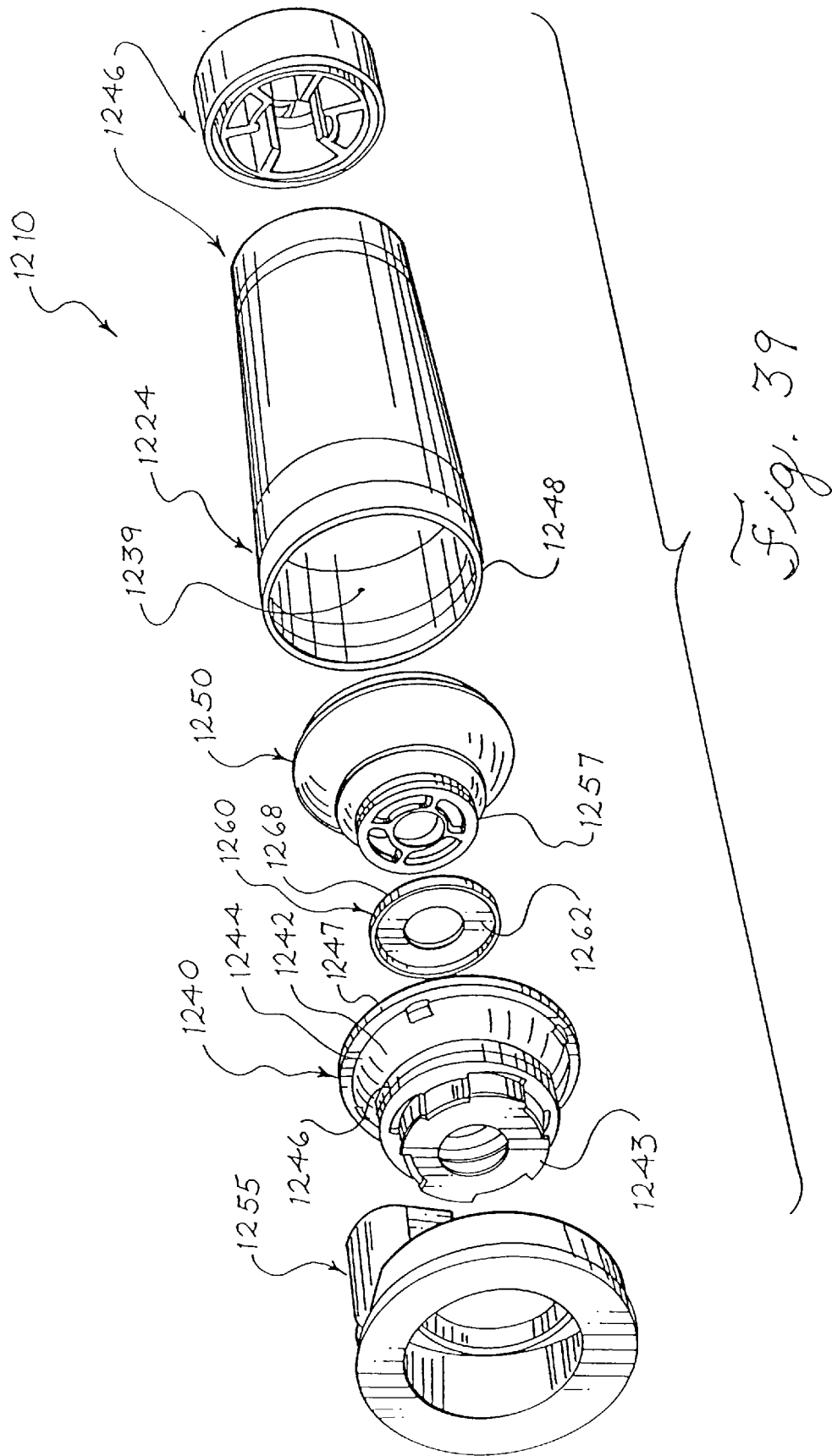

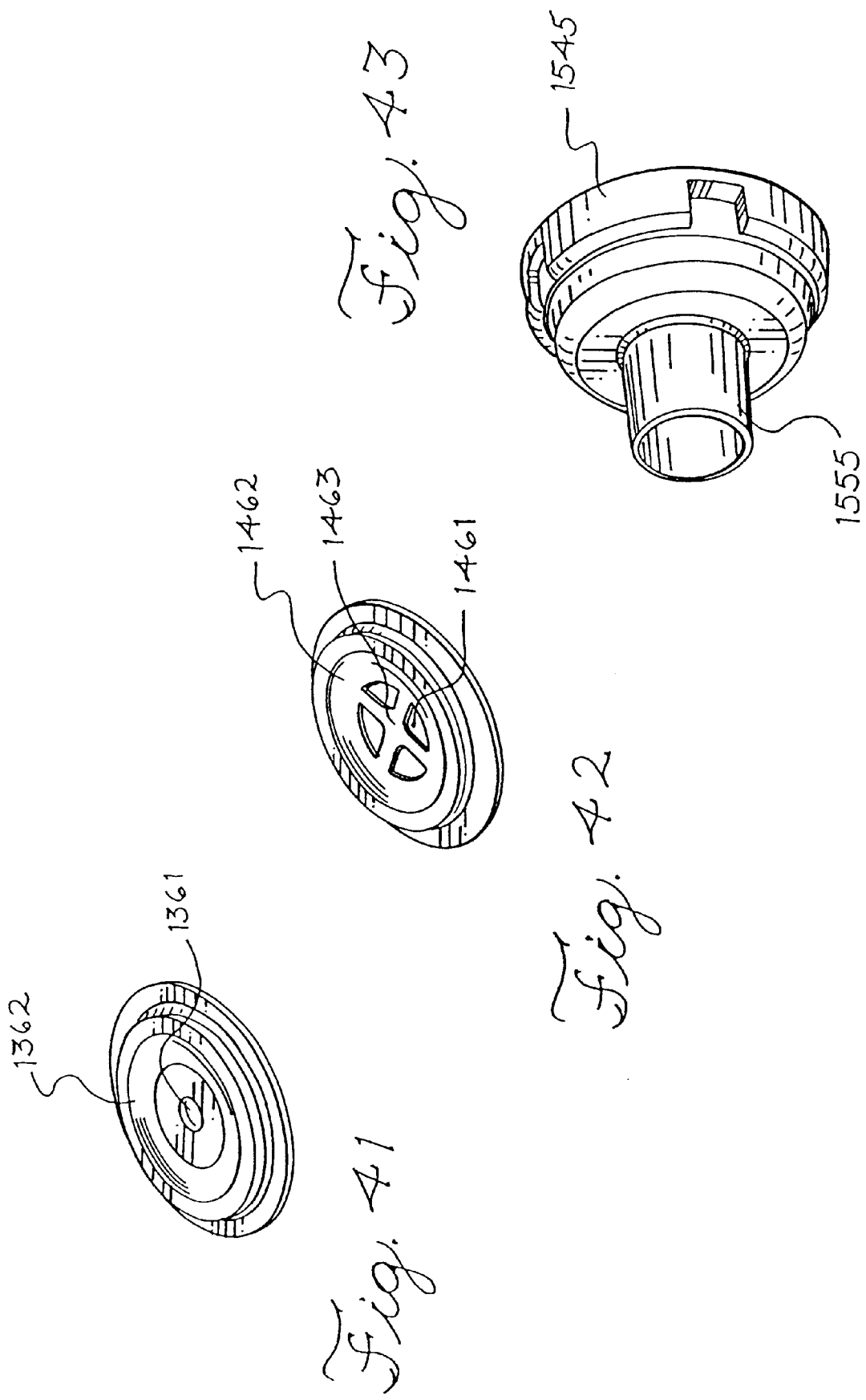

AEROSOL MEDICATION DELIVERY APPARATUS AND SYSTEM

RELATED APPLICATIONS

This application is a continuation-in-part of application Ser. No. 08/938,686 filed Sep. 26, 1997, which is incorporated herein by reference.

FIELD OF THE INVENTION

This invention relates to a portable aerosol medication delivery apparatus and system for administering a desired respirable dosage of a medication in aerosol form to a patient's lungs by oral inhalation.

BACKGROUND OF THE INVENTION

The use of aerosol medication delivery systems to administer medication in aerosol form to a patient's lungs by inhalation is well known in the art.

Conventional aerosol medication delivery systems include pressurized metered-dose inhalers (pMDIs). Conventional pMDIs typically have two components: a canister component in which the medication particles are stored under pressure in a suspension or solution form and a receptacle component used to hold and actuate the canister. The canister component typically includes a valved outlet from which the contents of the canister can be discharged. Aerosol medication is dispensed from the pMDI by applying a force on the canister component to push it into the receptacle component thereby opening the valved outlet and causing the medication particles to be conveyed from the valved outlet through the receptacle component and discharged from an outlet of the receptacle component. Upon discharge from the canister, the medication particles are "atomized" forming an aerosol. It is intended that the patient coordinate the discharge of aerosolized medication with his or her inhalation so that the medication particles are entrained in the patient's inspiratory flow and conveyed to the lungs. Typically, pMDIs have used propellants, such as chlorofluorocarbons (CFCs), to pressurize the contents of the canister and to propel the medication particles out of the outlet of the receptacle component.

Although conventional pMDIs have been widely used to provide many patients with the benefits of aerosol medication, conventional pMDIs have certain drawbacks. For example, an objective of aerosol therapy has been the optimization of the mass percentage of the respirable dose of an aerosol medication in order to optimize deposition in a patient's lungs to achieve a full therapeutic effect with the least possible side-effects. Conventional pMDIs may not have always been able to meet this objective.

One drawback associated with conventional pMDIs relates to the discharge velocity of the aerosol particles. Medication particles are stored under considerable pressure in the pMDI canister and as a consequence, their velocity may be high upon discharge.

Among other things, the effect of high velocity contributes to a significant number of aerosol medication particles impacting and depositing in the patient's oropharynx and upper airway rather than continuing their pathway through the upper airway and into the lungs. Such impaction and deposition may result in a significant portion of the medication dose being systemically absorbed or ingested. As documented in the literature [J. L. Rau, "Respiratory Care Pharmacology", 4$^{th}$ ed. (1994, Mosby) at pp. 256–261; K. Meeran, A. Hattersley, J. Burrin, R. Shiner, K. Ibbertson K., "Oral and Inhaled Corticosteroids Reduce Bone Formation as Shown by Plasma Osteocalcin Levels", *Am. J. Respir. Crit. Care Med* 151:333–336], systemic absorption or ingestion of aerosol medication may cause a patient adverse side-effects, particularly when the aerosol medication is a corticosteroid. Some of these adverse side-effects include pharyngeal candidiasis, hoarseness, and adrenal suppression.

The high velocity of the aerosol medication particles may also accentuate the difficulty of a significant number of patients, particularly the very young and elderly, to coordinate actuation of the pMDI with inhalation of the aerosol medication particles generated. Failure to coordinate the actuation and inhalation maneuvers and failure to inhale slowly, have been documented by the literature [S. P. Newman, "Aerosol Deposition Considerations in Inhalation Therapy" Chest/88/2/August, 1985/Supplement] as contributing to a significant reduction in the number of aerosol medication particles inspired and deposited in a patient's lungs.

Impaction and deposition of aerosol medication particles on a patient's oropharynx and upper airway may also contribute to an unpleasant taste in a patient's mouth, particularly with certain medication solution or suspension formulations such as flunisolide.

In addition to high particle velocity, a significant number of large non-respirable medication particles may be produced upon discharge as a result of the medication suspension or solution formulation as well as the atomization process. As mentioned above, conventional pMDIs have used CFCs to propel the medication out of the pMDI actuator outlet. In view of environmental concerns with CFCs, there has been a growing interest in using non-CFC propellants, such as hydrofluoroalkanes (HFAs).

An inhalation valve is often used in conjunction with an aerosol medication delivery apparatus to deliver a medication in an aerosol form to a user's respiratory tract. Typically, an inhalation valve is disposed at the output end of an aerosolization chamber and prevents aerosolized medication from leaving the chamber when the inhalation valve is in a closed position. When a patient inhales, the inhalation valve opens and allows the aerosolized medication to enter the patient's respiratory tract. The inhalation valve is usually designed to close upon exhalation by the patient.

Prior art inhalation valves generally consist of a valve member and a valve seat. In some types of prior art valves, the outer perimeter of the valve member seals against the valve seat. In operation, the act of inhalation causes the outer perimeter of the valve to move away from the valve seat and allow aerosolized medication to flow through to the patient.

In another type of prior art inhalation valve, the valve member includes one or more slits that define flaps on the valve member. Typically, the valve seat has a plurality of openings defined by what is known as a spider-like framework. In operation, when the patient inhales the flaps move away from the spider-like framework to allow aerosolized medication to pass through the openings to the patient. Upon exhalation, the flaps move against the framework to cover the openings. A number of advantageous improvements and modifications can be made to these prior designs.

It is another object to provide a device which reduces the need for a patient to coordinate activation of a pMDI canister with inhalation.

It is a further object to provide a device that reduces the delivery of nonrespirable medication particles from a pMDI canister to a patient.

It is yet another object to provide a device that reduces the impaction of medication particles on a patient's oropharynx and upper airway.

It is still another object to provide a device for the delivery of aerosol medication from a pMDI canister that uses an HFA propellant instead of a CFC propellant.

SUMMARY OF THE INVENTION

In order to address the above noted objectives, as well as other objectives, the present invention provides an improved aerosol medication delivery apparatus. The aerosol medication delivery apparatus includes a canister-holding portion and a chamber housing. The canister-holding portion has a receptacle for receipt of a pMDI canister containing a medication and a propellant. The canister-holding portion has a discharge orifice communicating with the receptacle to direct an aerosol into an interior of the chamber housing at an input end thereof. The chamber housing also has an output end from which medication can be withdrawn by inhalation by a patient. The canister-holding portion and the chamber housing are coupled together by a mechanism that provides for the canister-holding portion to be retracted into the chamber housing for storage. The coupling mechanism also allows the canister-holding portion to be extracted from its storage position in the chamber housing and pivoted into position for use when dispensing medication. According to one aspect of the present invention, the aerosol delivery system includes a containment baffle located at the output end of the chamber housing to partially block the output end.

Further in this aspect the containment baffle may be surrounded by an inhalation area including at least one opening and wherein the inhalation area is located concentrically with the containment baffle and the containment baffle is aligned with the discharge orifice. There may also be provided a backpiece located on the input end of the chamber housing, the backpiece including an opening located therein to receive a mouthpiece of an actuator boot of the pMDI canister. Also in this aspect the containment baffle may define an inhalation opening area located around a periphery thereof wherein the inhalation opening area has four arcuate-shaped openings, the containment baffle may be located at an upstream end of a mouthpiece extending from the output end of the chamber housing portion, the containment baffle may be located at a downstream end of a mouthpiece extending from the output end of the chamber housing portion. There may also be provided a receptacle coupled to the chamber housing at an upstream portion thereof; a well located in a bottom of the receptacle, the well communicating with the discharge orifice; and further wherein the chamber housing portion includes a first opening at the input end coupled to a ventilator circuit and a second opening at the output end leading to the patient. Further, the receptacle and chamber housing may be formed of an integrated unit.

According to another aspect, the aerosol medication delivery apparatus includes a canister-holding portion and a chamber housing. The canister-holding portion has a receptacle for receipt of a pMDI canister containing a medication and a propellant. The canister-holding portion has a discharge orifice communicating with the receptacle to direct an aerosol into an interior of the chamber housing at an input end thereof. The chamber housing also has an output end from which medication can be withdrawn by inhalation by a patient. The canister-holding portion and the chamber housing are coupled together by a mechanism that provides for the canister-holding portion to be retracted into the chamber housing for storage. The coupling mechanism also allows the canister-holding portion to be extracted from its storage position in the chamber housing and pivoted into position for use when dispensing medication. According to one aspect of the present invention, the aerosol delivery system includes a containment baffle located at the output end of the chamber housing to partially block the output end.

Further, in this aspect the containment baffle may be concave-like in shape as viewed from the interior space, the containment baffle may include at least one opening located concentrically adjacent thereto and the containment baffle may be aligned with the discharge orifice. Further in this aspect, there may be provided a pMDI canister of medication having a stem, wherein the canister is located at least in part within the receptacle. Also the canister may contain HFA, the medication may include flunisolide, the containment baffle may be convex-like in shape as viewed from the interior space, the chamber housing may have squared-off sides, the containment baffle may define an inhalation opening area located around a periphery thereof, the inhalation opening area may have four arcuate-shaped openings. In this aspect the containment baffle may have a solid center portion located along a central axis of the chamber housing, the containment baffle may have a center portion having a plurality of openings formed through a periphery thereof, the containment baffle may have a screen-like mesh defining a plurality of openings therethrough. Also in this aspect, the ambient air can pass into the interior space when a pMDI canister is located in the canister-holding portion, the containment baffle may have a curved top and bottom sides and straight vertical sides, the containment baffle may include a center portion coupled to the chamber housing by a plurality of ribs, the containment baffle may be located at an upstream end of a mouthpiece extending from the output end of the chamber housing portion, the containment baffle may be located at a downstream end of a mouthpiece extending from the output end of the chamber housing portion. Further in this aspect there may be provided a mechanism coupling the canister-holding portion and the chamber housing providing for the canister-holding portion to be retracted into the chamber housing for storage and to be extended out of the chamber housing and pivoted into position for use in dispensing medication.

In another aspect, an aerosol medication delivery apparatus includes a canister-holding portion including a receptacle for receipt therein of a pMDI canister, wherein the pMDI canister has medication and a propellant contained therein under pressure, the canister-holding portion having a discharge orifice communicating with the receptacle to receive the medication and propellant from the pMDI canister; a chamber housing having an input end and an output end from which medication can be withdrawn by a patient, the chamber housing defining an interior space wherein the discharge orifice of the canister-holding portion communicates with the interior space at the input end; a mechanism coupling the canister-holding portion and the chamber housing providing for the canister-holding portion to be retracted into the chamber housing for storage and to be extended out of the chamber housing and pivoted into position for use in dispensing medication; and a containment baffle located at the output end to partially block the open output end.

In addition, in this aspect the containment baffle may be concave-like in shape as viewed from the interior space. Further, in this aspect containment baffle may include at least one inhalation opening area located concentrically adjacent thereto, the containment baffle may be axially aligned with the discharge orifice. This aspect may provide a pMDI canister of medication having a stem, wherein the canister is located at least in part within the receptacle, the canister may contain HFA and the medication may include flunisolide. Also in this aspect the containment baffle may define an inhalation opening area located around a periphery thereof, the inhalation opening area may include four arcuate-shaped openings, the containment baffle may include a solid center portion located along a central axis of the chamber housing. In addition, in this aspect ambient air may pass into the interior space when a pMDI canister is located in the canister-holding portion, the containment baffle may have a curved top and bottom sides and straight vertical sides and the containment baffle may be located at a downstream end of a mouthpiece extending from the output end of the chamber housing portion.

In another aspect, an aerosol medication delivery apparatus includes a chamber housing with an input end an output end. The input end receives the discharge of a medication from a pMDI canister and the output end includes a containment baffle that partially blocks the output end. The pMDI canister is received in an elastomeric backpiece that is adapted to accommodate various sizes of actuator boot mouthpieces.

In another aspect, the invention provides an aerosol medication delivery apparatus for use with a pMDI canister having medication and a propellant contained therein under pressure, wherein the pMDI canister has a discharge orifice from which the medication and propellant can be discharged forming an aerosol. The apparatus has a chamber housing having an input end and an output end and defining an interior space, wherein the input end receives the medication discharged from the discharge orifice of the pMDI canister into the interior space and wherein the medication can be withdrawn from the interior space by inhalation by a patient from the output end. The aerosol medication delivery apparatus also includes a valve at the output end. The valve has a valve seat and a valve member. The valve seat has a sealing surface and the valve member has a central open area and a sealing portion at the perimeter of the central open area that mates with the sealing surface when the valve is closed. The valve allows medication to be withdrawn through the central open area but prevents backflow into the chamber housing.

This aspect of the present invention may also be provided with a containment baffle located at the output end. Also the sealing surface may be formed on the outer perimeter of the containment baffle, the containment baffle may be dome shaped and include a concave surface and a convex surface, wherein the convex surface faces downstream and the concave surface faces toward the input end of the chamber. This aspect of the invention may further be provided with a retainer defining a channel near the output end, an engaging member located on the valve member, wherein the engaging member is movable between a first position and a second position within the channel. In addition, the convex surface may face toward the input end of the chamber housing, the central open area may be circular shaped, the valve member may have an inner portion, an outer portion and an engaging member, inhalation openings are located near the output end and are defined between the containment baffle and the chamber housing. This aspect of the invention may further be provided with a protrusion formed near the output end on the outer surface of the chamber housing. Also, in this aspect the inner portion may be positioned adjacent the inhalation openings; the engagement member may concentrically surround the protrusion, the valve member may be dome shaped in cross section, the apparatus may also include a downstream portion attached with the output end wherein the downstream portion has an inner surface and a plurality of retaining ribs spaced apart from the inner surface. The retaining ribs define gaps which permit exhaled air to flow through to the atmosphere. The present invention may further be provided with a valve member that is made of a rigid material and the sealing portion may form a continuous surface.

In another aspect, the invention provides an aerosol medication delivery apparatus for use with a pMDI canister having medication and a propellant contained therein under pressure, wherein the pMDI canister has a discharge orifice from which the medication and propellant can be discharged forming an aerosol. The apparatus has a chamber housing having an input end and an output end and defining an interior space, wherein the input end receives the medication discharged from the discharge orifice of the pMDI canister into the interior space and wherein the medication can be withdrawn from the interior space by inhalation by a patient from the output end. The apparatus includes a mouthpiece operatively attached to the output end; and a valve located near the output end having a valve seat having a sealing surface and a valve member having an inner portion and an outer portion. The inner portion has a central open area and a sealing portion at the perimeter of the central open area that mates with the sealing surface when the valve is closed, wherein the inner portion allows medication to be withdrawn through the central opening but prevents backflow into the chamber housing. The outer portion is located in a peripheral opening defined between the chamber housing and the mouthpiece, the outer portion operates to prevent air flow through the peripheral opening upon patient inhalation but which permits air flow through the peripheral opening upon exhalation into the mouthpiece.

Further, in this aspect of the invention there may be provided a containment baffle located at the output end to partially block the output end and the sealing surface may be located at the periphery of the containment baffle.

In another aspect, the invention provides an aerosol medication delivery apparatus for use with a pMDI canister having medication and a propellant contained therein under pressure, wherein the pMDI canister has a discharge orifice from which the medication and propellant can be discharged forming an aerosol. The apparatus has a chamber housing having an input end and an output end and defining an interior space, wherein the input end receives the medication discharged from the discharge orifice of the pMDI canister into the interior space and wherein the medication can be withdrawn from the interior space by inhalation by a patient from the output end. The aerosol medication delivery apparatus also includes a valve at the output end. The valve has a valve seat and a valve member. The valve seat has a sealing surface and the valve member has a central open area and a sealing portion at the perimeter of the central open area that mates with the sealing surface when the valve is closed. An engagement member is located on the valve member. The valve allows medication to be withdrawn through the central open area but prevents backflow into the chamber housing.

Further in this aspect of the invention the valve member may have an inner portion, the engagement member may include an input side and an output side, a downstream portion may be attached to the output end, a mouthpiece may be attached to the downstream portion, an inner surface of the downstream portion may define a recess, the output side of the engagement member may be disposed in the recess, the central open area may be circular shaped, the diameter of the chamber housing gradually increases from the input end to the output end, a baffle member may be attached to the output end, a receiving member may be formed on a downstream end of the baffle member, the input side of the engaging member may be concentrically disposed around the receiving member, a mask may be attached to the output end. Further in this aspect, the sealing portion may form a continuous surface.

In another aspect, the invention provides a method for delivering aerosol medication to a patient including the following steps: providing a pMDI canister having medication and a propellant contained therein under pressure, wherein the pMDI canister has a discharge orifice; providing a chamber housing having an input end and an output end and defining an interior space, wherein the input end receives the medication discharged from the orifice of the pMDI canister into the interior space and wherein the medication can be withdrawn from the interior space by inhalation by a patient from the output end; providing a valve at the output end including a valve seat and a valve member, the valve seat having a sealing surface and the valve member having a central open area and a sealing portion at the perimeter of the central open area; depressing the pMDI canister; discharging medication and propellant out from the discharge orifice; forming an aerosolized medication; passing aerosolized medication through the chamber housing and to the patient.

In another aspect the invention provides an aerosol medication delivery apparatus for use with a pMDI canister having medication and a propellant contained therein under pressure, wherein the pMDI canister has a discharge orifice from which the medication and propellant can be discharged forming an aerosol, the apparatus includes a chamber housing having an input end and an output end and defining an interior space, wherein the input end receives the medication discharged from the discharge orifice of the pMDI canister into the interior space and wherein the medication can be withdrawn from the interior space by inhalation by a patient from the output end; means for sealing the chamber housing having a base and a movable member movable between an open position and a closed position, the movable member having a central open area. The means for sealing the chamber housing allows medication to be withdrawn through said central open area when the movable member is in the open position but prevents backflow into the chamber housing when the movable member is in the closed position.

The invention provides the foregoing and other features, and the advantages of the invention will become further apparent from the following detailed description of the presently preferred embodiments, read in conjunction with the accompanying drawings. The detailed description and drawings are merely illustrative of the invention and do not limit the scope of the invention, which is defined by the appended claims and equivalents thereof.

BRIEF DESCRIPTION OF THE DRAWINGS

FIG. 1 is a perspective view of an aerosol medication delivery system in accordance with an embodiment of the present invention.

FIG. 2 is an exploded view of the aerosol medication delivery system of FIG. 1.

FIG. 3 is a side view of the aerosol medication delivery system of FIG. 1.

FIG. 4 is a side sectional view of the aerosol medication delivery system of FIG. 1.

FIG. 5 is a front view of the canister-holding portion shown in FIG. 1.

FIG. 6 is a sectional view of the canister-holding portion of FIG. 5 taken along line 6–6'.

FIG. 11 is an enlarged sectional view of an inside upstream portion of the chamber housing of FIG. 1 showing part of the coupling mechanism.

FIG. 12 is a perspective view of an aerosol medication delivery system in accordance with another embodiment of the present invention.

FIG. 13 is an end view of the embodiment of FIG. 12.

FIGS. 14–16 each show an end view of an alternative embodiment of the containment baffle shown in FIG. 8.

FIG. 17 is a side sectional view of another alternative embodiment of the aerosol medication delivery apparatus of FIG. 1.

FIG. 18 is a end view of the embodiment shown in FIG. 17

FIG. 19 is a side sectional view of yet another alternative embodiment of the aerosol medication delivery apparatus of FIG. 1.

FIG. 20 is an end view of the containment baffle of the embodiment of FIG. 19.

FIG. 21 is a side sectional view of yet another alternative embodiment of the aerosol medication delivery apparatus of FIG. 1.

FIG. 22 is an end view of the containment baffle of the embodiment of FIG. 21.

FIG. 23 is an exploded perspective view of an aerosol medication delivery system in accordance with another embodiment of the present invention.

FIG. 24 is a sectional view of the embodiment of FIG. 23.

FIG. 25 is a sectional view of the embodiment of FIG. 23.

FIG. 26 is an exploded perspective view of yet another alternative embodiment of aerosol medication delivery apparatus of FIG. 1.

FIG. 27 is a front view of a valve member used in the embodiment of the invention shown in FIG. 26.

FIG. 28 is a sectional view taken along line 28—28 of FIG. 27.

FIG. 29 is a perspective view of a mouth piece used in the embodiment of the invention shown in FIG. 26.

FIG. 33 is an exploded perspective view of yet another alternative embodiment of the aerosol medication delivery apparatus of FIG. 1.

FIG. 34 is a side sectional view of the embodiment of FIG. 33.

FIG. 37 is a side sectional view of another alternative embodiment of the aerosol medication delivery apparatus of FIG. 1.

FIG. 38 is a perspective view of an attachment member used in the embodiment shown in FIG. 37.

FIG. 39 is an exploded perspective view of yet another alternative embodiment of the aerosol medications of the apparatus of FIG. 1.

FIG. 41 shows an alternative embodiment of a valve member for use with the present invention.

FIG. 42 shows another alternative embodiment of a valve member for use with the present invention.

FIG. 43 shows an alternative embodiment of a mouth piece for use with the present invention.

DETAILED DESCRIPTION OF THE PRESENTLY PREFERRED EMBODIMENTS

I. General

Figure 7:
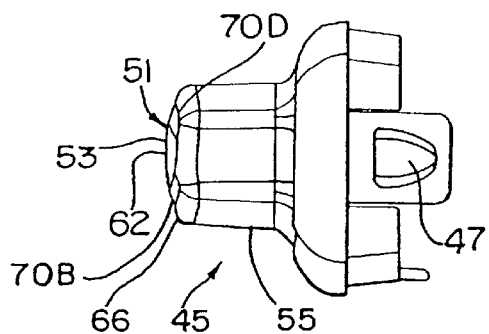
FIG. 7 is a side view of the downstream housing portion in FIG. 1.

FIGS. 1–11 show an embodiment of an aerosol medication delivery apparatus 10. The apparatus 10 comprises a pMDI canister-holding portion (or dispenser) 22 coupled to a chamber housing portion 24. The delivery apparatus 10 together with a pMDI canister 30 form an aerosol therapy system 12.

The canister-holding portion 22 has a generally rectangular cross-sectional shape that defines a receiving area or receptacle 28 for receipt therein of the pMDI canister 30. The receiving area 28 is suited for conventional pMDI canisters of well-known construction. The pMDI canister 30 contains a medication suspension or solution under pressure. In the present embodiment, an HFA propelled medication suspension or solution formulation is used. In one embodiment, the liquid medication is flunisolide. Other propellants and other medications may also be used.

Referring to FIG. 6, the pMDI canister 30 has a stem 32 that permits a portion of the medication suspension or solution to be discharged therefrom upon application of a force on the stem 32. When the pMDI canister 30 is located in the receiving area 28 of the canister-holding portion 22, the canister stem 32 is positioned in a vertical channel or well 34 formed in the bottom of the canister-holding portion 22. When the stem 32 of the canister 30 is located in the vertical channel 34, ambient air can pass into the chamber via a passageway 33. A horizontal passage 35 communicates with the vertical channel 34. The horizontal passage 35 leads to a discharge orifice 36 located opposite from the vertical channel 34.

II. Chamber Housing

Referring to FIG. 6, the discharge orifice 36 forms the passage by which medication particles from the pMDI canister 30 can exit the canister holding portion 22 and enter into the chamber housing portion 24. The chamber housing 24 has an input end 46 and an output end 48 that define the ends of an interior space 39.

Referring to FIGS. 2–4, in a present embodiment, the chamber housing portion 24 is formed of two parts: a main housing portion 43 and a downstream portion 45. The main housing portion 43 and the downstream portion 45 together define the interior space 39 of the chamber housing portion 24. The downstream portion 45 has retaining fingers 47 that engage in slots 49 on each side of the main housing portion 43. In the embodiment shown, the main housing portion 43 and the downstream portion 45 easily snap together and can be easily disconnected for cleaning.

Referring to FIG. 2, the main housing portion 43 has a curved cross section. In a present embodiment, the curved cross-section has a complex geometry formed of a plurality of radii to form a convenient, easy-to-use shape.

III. Containment Baffle/Mouthpiece

Referring to FIGS. 2 and 7–9, a containment baffle 51 is located in the downstream portion 45 at the outlet of the chamber housing 24. The containment baffle 51 is located centrally and forms a distal wall 53 of the downstream portion 45. The containment baffle 51 is positioned so as to partially block the output end 48. The containment baffle 51 reduces the velocity or flow rate or both of the aerosol medication particles on axis 42 of the chamber housing 24. A mouthpiece 55 is located on the outside of the downstream portion 45 and includes the containment baffle 51 at an outlet end thereof.

Figure 8:
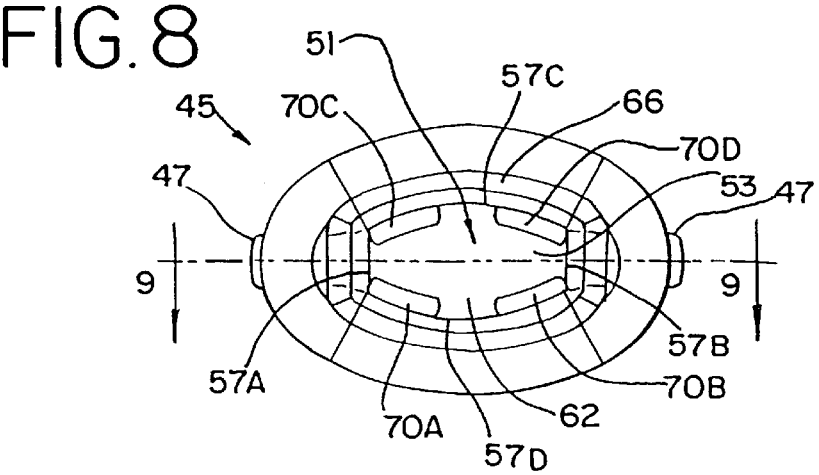
FIG. 8 is an end view of the downstream housing portion shown in FIG. 7.
Figure 9:
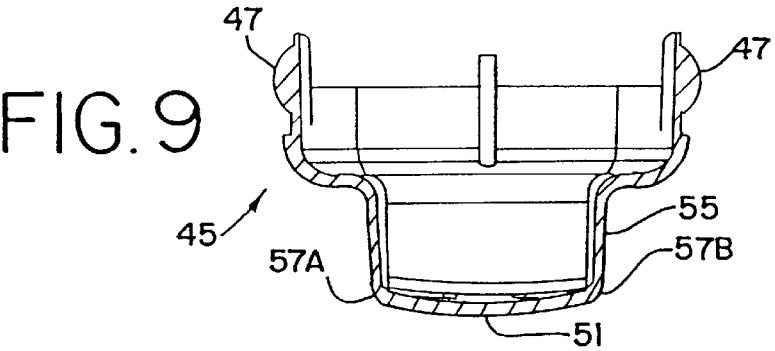
FIG. 9 is a sectional view of the downstream housing portion shown in FIG. 8 taken along line 9–9'.

As shown in FIGS. 7–9, the containment baffle 51 has a concave-shaped center portion 62. In the embodiment shown, the perimeter of the concave-shaped center portion 62 of the containment baffle 51 has generally straight vertical sides 57A and 57B, a curved top side 57C. and a curved bottom side 57D. The perimeter of the concave-shaped center portion 62 of the containment baffle 51 conforms generally in shape to the cross-sectional shape of the mouthpiece 55. The concave-shaped center portion 62 of the containment baffle 51 is aligned with a central axis 42 of the chamber housing 24 and is directly in line with the discharge orifice 36. Aerosol medication particles that have a flow path away from the axis of symmetry 42 tend to have a velocity that is lower than that of particles near to the axis of symmetry. The center portion 62 of the containment baffle 51 reduces the forward, on-axis velocity and simultaneously acts as an impaction surface for on-axis projectile aerosol medication particles. At the same time the center portion 62 allows slower moving aerosol medication particles to migrate towards the sides 52 of the chamber housing 24. The forward velocity of the aerosol medication particles away from the axis 42 along the chamber length is also reduced by the outer portion 66 of the containment baffle 51 that is concentric with the concave shaped center portion 62.

Positioned between the center and outer portions 62 and 66 is an inhalation opening area 70. In the embodiment, the inhalation opening area 70 is defined by four openings 70A–70D. The openings are arcuate in shape and conform to the periphery of the central portion 62. Each of the openings 70 has a length of approximately 9 mm and a width of approximately 2 mm. The size, shape and number of openings may vary depending on the medication suspension or solution formulation and/or propellant used.

In a present embodiment, the aerosol delivery apparatus 10 includes a cap 74 which can be placed over the mouthpiece 55 to prevent contaminants from entering the interior space 39. The cap 74 serves to protect the mouthpiece 55 and keep it relatively clean.

IV. Operation

To use the aerosol delivery apparatus 10 for delivery of an aerosol medication, the canister-holding portion 22 and chamber housing 24 are arranged as shown in FIG. 1. The cap 74 is removed and the pMDI canister 30 is located in the receiving area 28 with the stem 32 inserted into the channel 34 formed in the bottom of the receiving area 28 as shown in FIG. 6. As mentioned above, the apparatus 10 receives the pMDI canister 30 which is operated conventionally (i.e. by pressing down on the pMDI canister 30 which is located stem-side-down in the receiving area 28). Upon depression of the stem 32, the medication suspension or solution formulation in the pMDI canister 30 is discharged out of an opening 33 at the tip of the stem 32. As the medication suspension or solution formulation flows through the horizontal channel 35 and out of the discharge orifice 36, the propellant and suspending liquid or solvent evaporate and the medication particles are discharged in aerosol form into the surrounding environment inside the chamber volume 39. Upon discharge from the pMDI canister 30, the medication particles in the aerosol plume may have an average speed, size distribution and/or flow rate that may not be ideal for direct inhalation by a patient. However, once the aerosol medication is inside the chamber volume 39, the proportion of larger non-respirable particles available on inhalation is minimized and the dose of respirable particles is optimized. The aerosol medication particles are withdrawn therefrom by having the patient, whose mouth is around the mouthpiece 55, inhale through the inhalation opening area 70. The aerosol medication particles will then flow through the inhalation opening area 70 and into the patient's mouth.

V. Retraction for Storage

Figure 10:
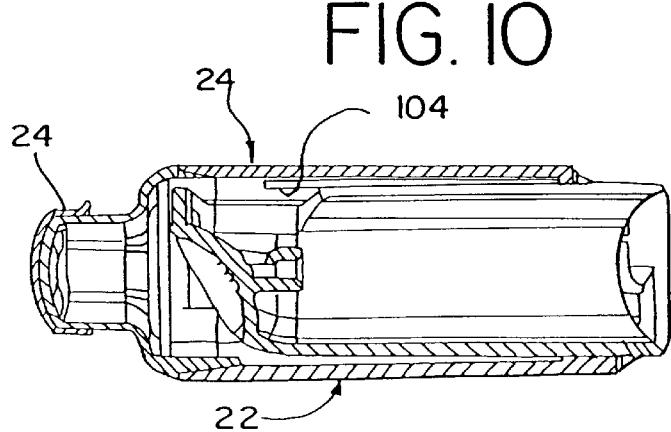
FIG. 10 is a sectional view of the embodiment in FIG. 1 in a retracted position.

A further feature of the aerosol medication apparatus 10 is that it can be retracted for convenient storage and portability. For this purpose, the chamber housing 24 is coupled to the canister-holding portion 22 via a coupling mechanism 94 as shown in FIG. 11. The coupling mechanism 94 permits the aerosol medication delivery apparatus 10 to be compactly stored by pivoting the canister-holding portion 22 from the position of FIGS. 1–4 to a horizontal position and then pushing the canister-holding portion 22 so that it translationally moves into the chamber housing 24 as shown in FIG. 10.

Referring to FIG. 11, the pivoting and translational movement is accomplished by the structure of the coupling mechanism 94. In particular, the coupling mechanism 94 includes a pair of slots 96 formed in the chamber housing 24, wherein each slot 96 has an open end 98 and a closed end 100. As shown in FIG. 5, the canister-holding portion 22 has a pair of pegs 102, attached thereto. In addition, the interior portion of the chamber housing 24 has multiple parallel tracks 104 (shown in FIG. 10) which guide the canister-holding portion 22 into the chamber housing 24. Alternatively, instead of parallel tracks a retaining structure (not shown) may be formed inside the upstream portion of the chamber housing 24. The retaining structure includes slots to receive the pegs 102 to guide the canister-holding portion 22 into the chamber housing 24.

To connect the chamber housing 24 and the canister-holding portion 22 together, a top end 109 of the canister-holding portion 22 is first inserted into the output end 48 of the chamber housing 24 and translationally moved towards and past the input end 46 so that the pegs 102 are inserted into the open ends 98 of the corresponding slots 96. Each of the pegs 102 can then translationally move within its respective slot 96 to the closed end 100 thereof. Thus, the canister-holding portion 22 is telescopically received within the chamber housing 24 during translational movement and is able to move from the retracted position of FIG. 10 to an extended position. At the extended position, both pegs 102 contact the closed ends 100 of their corresponding slots 96 and the canister-holding portion 22 is then allowed to pivot to the position of FIG. 4 so that the patient can use the apparatus 10. The end of the canister-holding portion 22 is curved so as to allow it to pivot relative to the chamber housing 24. The foregoing coupling and retraction mechanism allow for easy use, transport, and lower manufacturing costs.

To facilitate handling by the patient, a plurality of ribs 77 may be located along the front and rear sides of the canister-holding portion 22 close to the top edge 109 thereof. These ribs 77 remain exposed when the canister-holding portion 22 is retracted into the chamber portion 24 so that the patient can use these ribs to help grip the end of the canister-holding portion 22 in order to withdraw it from the chamber portion 24. After use by the patient, the cap 74 can be placed back over the mouthpiece 55.

VI. Advantages of Disclosed Embodiment

With the embodiment disclosed above, the end result of combining the specified inhalation opening area 70, the chamber housing 24, and the containment baffle 51 is to administer a controllable and desired respirable dose of aerosol medication to a patient for inhalation into the lungs. Further, the disclosed embodiment provides advantages over prior devices in that it incorporates an integrated actuator and is easier to use and is easier to store and carry given its smaller size.

An advantageous feature of the disclosed embodiment is provided by the containment baffle 51. As mentioned above, the velocity of the aerosol medication particles nearest the axis of symmetry 42 will typically be greater than that of aerosol medication particles that are located further from the axis 42. The velocity of the aerosol medication particles near the axis 42 may be so large as to reduce the effectiveness of delivering the medication to the patient because it will cause a significant portion of the aerosol medication particles to impact on the oropharyngeal region and upper airway where they have no therapeutic value and, in the case of medication such as corticosteroids, may give rise to adverse side-effects. The containment baffle 51 overcomes this potential problem by isolating the patient's mouth from the location at which the greatest risk of high velocity impaction may occur. The containment baffle provides this solution in a manner that is relatively inexpensive and easy to manufacture.

The disclosed aerosol medication delivery apparatus optimizes the deposition of respirable aerosol medication particles in a patient's lungs to provide a desired therapeutic effect. The aerosol medication delivery apparatus also reduces the importance of coordination between the actuation and inhalation maneuvers and reduces or eliminates possible side-effects caused by aerosol medication formulations consisting of corticosteroids. The aerosol medication delivery apparatus also reduces or eliminates the unpleasant taste associated with aerosol medication formulations such as flunisolide and allows for convenient portability and quick use.

In the case of pMDIs that use HFA as a propellant for flunisolide, the present embodiment provides a particular advantage. Through use of the present embodiment, the respirable dosage of flunisolide delivered to the patient can be controlled in a manner to closely conform to the dosage of flunisolide that had been delivered using conventional prior art systems that used prior propellants, such as CFC. In this manner, the dosage of flunisolide can be consistently maintained, thereby benefiting administration of such medication to patients.

The shape, size, and number of openings in the inhalation opening area may vary in order to ensure the administration of a desired respirable dose of a specific pMDI formulation. Upon discharge the on-axis aerosol medication particles, which are generally non-respirable and have a higher inertia than the respirable particles, collide with the interior center portion of the containment baffle resulting in a reduction in the number of larger (non-respirable) aerosol medication particles, and the division of larger (non-respirable) aerosol medication particles into smaller respirable particles.

By sealing off (except for the inhalation opening area) the output end of the chamber, the containment baffle contributes to maintaining a high pressure zone in the chamber which allows for the deflection of most slower moving respirable aerosol medication particles away from the containment baffle and into the chamber for containment until inhaled by the patient through the inhalation opening area. The containment of the respirable aerosol medication particles in the chamber provides the patient with more time to inhale the aerosol medication particles and, therefore, reduces the importance of exact coordination between the discharge maneuver and inhalation.

VII. Exemplary Embodiment

In one exemplary embodiment, shown in FIGS. 1–11, the canister-holding portion 22 is approximately 7.5 cm in height and is approximately 2.5 by 2.5 cm in cross section. The chamber housing 24 is approximately 8 cm in length and has an oval-shaped cross section with dimensions of approximately 49 mm by 33 mm. The mouthpiece 55 is approximately 1.5 cm in length. The canister-holding portion, the chamber housing, and the end cap are formed of a suitable hard, durable plastic, such as polypropylene. The discharge orifice 36 has a diameter of approximately 0.011 inches. In a present embodiment, the containment baffle 51 has a width of approximately 27 mm and a height of approximately 15 mm at the center and 5 mm at the side edges.

For purposes of this embodiment, it is assumed that the pMDI canister contains a 0.06% w/v to 0.24% w/v mixture of liquid medication, such as flunisolide in ethanolic solution and HFA as a propellant. Alternatively, the pMDI canister may contain a formulation of medication that uses CFC as a propellant. It is understood that the pMDI canister 30 can also contain other liquids and other mixtures without departing from the spirit of the invention.

VIII. Alternative Embodiments

Referring to FIGS. 12 and 13, another embodiment of an aerosol delivery apparatus 110 is shown. This embodiment is similar to the embodiment shown in FIGS. 1–11 and like components are labeled with the same numerals. In the embodiment of FIGS. 12 and 13, the containment baffle 151 is located at an upstream end of the passageway defined in the mouthpiece 55. The containment baffle 151 in this embodiment is convex in shape and diverts flow around an on-axis trajectory. In the embodiment of FIGS. 12 and 13, a chamber housing 124 has four squared-off sides 125, 126, 127, and 128. The squared-off sides may facilitate gripping of the device.

Referring to FIGS. 14–16, there are depicted alternative embodiments of the containment baffle. In FIG. 14, a containment baffle 251 has a screen-like structure forming a plurality of openings defined between a crisscrossed mesh 252. The surface area provided by the mesh 252, combined with the relatively small areas of the openings, serves to prevent aerosol particles having a high velocity from passing to the patient. In FIG. 15, a containment baffle 351 has a plurality of small circular openings formed around a periphery of a solid central portion 362. Like the previous embodiments, the embodiment of FIG. 15 provides a surface area 362, combined with the relatively small openings, serves to prevent aerosol particles having a high velocity from passing to the patient. In FIG. 16, a containment baffle 451 has four relatively large openings formed around the periphery a solid dish-shaped central portion 462. The dish-shaped central portion 462 is connected to the remainder of the chamber body by one or more ribs 463. Like the previous embodiments, the embodiment of FIG. 16 provides a surface area 462, that serves to prevent aerosol particles having a high velocity from passing to the patient.

Referring to FIGS. 17 and 18, there is shown an alternate embodiment 512 of an aerosol delivery apparatus. The embodiment of FIGS. 17 and 18 includes an aerosol delivery apparatus 510. The apparatus 510 includes a chamber housing 524 which defines an interior space 539. The apparatus 510 does not include an integrated canister-holding portion. Instead, the chamber housing 524 has a backpiece 527. The backpiece 527 is made of an elastomeric material and is fitted over the upstream end of the chamber housing 524. The backpiece 527 has an opening 529 located centrally therein. The opening 529 is sized to receive the mouthpiece end of a separate pMDI actuator boot. In a preferred embodiment, the opening 529 is sized so that the mouthpiece of the pMDI actuator boot fits snugly into the opening 529. Because the backpiece 527 is formed of an elastomeric material, it is resilient and the opening 529 in the backpiece can be stretched, thereby enabling it accommodate actuator boot mouthpieces of various sizes and shapes. The backpiece 527 may be similar to the backpiece described in U.S. Pat. No. 4,470,412 or in U.S. Pat. No. 5,848,588, the entire disclosure of which is incorporated by reference herein.

Located at a downstream end of the chamber housing 524 is a mouthpiece 555. Also located at the downstream end of the chamber housing 524 is a containment baffle 551. The containment baffle 551 may be similar to the containment baffle 51 in the above described embodiment. Located around the periphery of the containment baffle center portion 562 is an inhalation opening area 570. The inhalation opening area 570 includes four arcuate shaped openings. In the embodiment of FIGS. 17 and 18, the containment baffle 551 is located at the downstream end of the mouthpiece 555, although in alternative embodiments, the containment baffle may be located at the upstream end of the mouthpiece or anywhere along the length of the mouthpiece.

With the embodiment of FIGS. 17 and 18, the patient inserts the actuator boot mouthpiece into the opening 529 and inserts the pMDI canister into the actuator boot. The patient presses down on the pMDI canister to cause a plume of aerosol medication to be discharged from the stem of the pMDI canister out of the mouthpiece of the actuator boot and into the interior space 539. The patient inhales the aerosol from the interior space 539 via the mouthpiece 555 of the apparatus 510.

Another embodiment of the aerosol medication delivery apparatus is shown in FIGS. 19 and 20. An aerosol delivery apparatus 610 includes a chamber housing 624 defining an interior space 639. The apparatus 610 also includes an elastomeric backpiece 627 which may be similar to the backpiece in the embodiment shown in FIGS. 17 and 18. The apparatus 610 includes a containment baffle 651. The containment baffle 651 is located at the downstream end of the chamber housing 624 just upstream of the mouthpiece 655. The containment baffle 651 includes an inhalation opening area 670 located around the periphery of the containment baffle 651. In the embodiment of FIGS. 19 and 20, the containment baffle 651 may be formed of a single piece of material with the chamber housing 624. The mouthpiece 655 may be formed of a separate piece of material that is coupled to the downstream end of the chamber housing 624.

The embodiment of FIGS. 19 and 20 may be used in a similar manner as the embodiment of FIGS. 17 and 18.

Still another embodiment of the aerosol medication delivery apparatus is shown in FIGS. 21 and 22. This embodiment of the aerosol delivery apparatus is particularly suited for use by a mechanically ventilated patient (i.e. a patient using a ventilator). In FIG. 21, an aerosol delivery apparatus 710 includes components that are similar to the previous embodiments, in particular the embodiment of FIGS. 17 and 18. A chamber housing 724 defines an interior space 739. The apparatus 710 is intended to be positioned in a ventilator circuit, in particular in the air passageway that provides inspiratory air flow from a ventilator to the patient. The chamber housing 724 includes a first opening 727 located in a first tubular extension 728 extending from the upstream end 746 of the chamber housing 724 and a second opening 755 located in a second tubular extension 756 that extends from the downstream end 748 of the chamber housing 724. The first opening 727 connects to tubing 731 that leads to the ventilator (not shown) and the second opening 755 leads to tubing, a mask, a mouthpiece, or other suitable means (not shown) of providing air from the ventilator to the patient. Located at the upstream end of the chamber 724 is a receptacle 722. At the bottom of the receptacle 722 is a well 734 adapted to receive the stem of a pMDI canister. The well 734 extends into a rib 735 that extends across the entrance into the interior space 739 of the chamber housing 724. The rib 735 may be located at or along the extension 728. The rib 735 includes a discharge opening 736 that communicates with the well 734. The discharge opening 736 is oriented toward the interior space 739. The receptacle 722, the rib 735, and the discharge opening 736 are integrated with the chamber housing 724 forming part of the aerosol delivery apparatus 710, (i.e. the receptacle and chamber housing form an integrated unit). In one embodiment the receptacle 722, the rib 735, and the discharge opening 736 are formed of the same piece of material as the chamber housing 724, or alternatively, they may be formed of separate pieces. Further disclosure regarding an integrated chamber housing and canister receptacle is included in U.S. Pat. No. 5,012,804.

Located at the downstream end 748 of the chamber 724 is a containment baffle 751. The containment baffle 751 may be located at the downstream end of the chamber housing 724 or along the extension 756. The containment baffle 751 includes an inhalation opening area 770 located around the periphery of the containment baffle 751.

The embodiment of FIGS. 21 and 22 may be used in a similar manner as the device disclosed in U.S. Pat. No. 5,012,804. The apparatus 710 may be positioned in the inspiratory flow path from the ventilator to the patient when the patient is initially placed on the ventilator. The apparatus 710 is then left in place until needed. Alternatively, the apparatus 710 may be positioned in the inspiratory flow path of the ventilator circuit just prior to when a dose of aerosol medication is to be delivered to a ventilated patient. A pMDI canister is positioned in the receptacle 722 and actuated. The medication from the pMDI canister is conveyed with the inspiratory flow from the ventilator to the patient. As in the previously described embodiments, the containment baffle 751 reduces on-axis non-respirable particles.

Another embodiment of the aerosol medication delivery apparatus is shown in FIGS. 23–25. In FIG. 23, an aerosol delivery apparatus 810 includes components that are similar to the previous embodiments, in particular the embodiments shown in FIGS. 1–13. A chamber housing 824 has an input end 846 and an output end 848 that define the ends of an interior space 839. The chamber housing 824 is formed of a main housing portion 843 and a downstream portion 845 that together define the interior space 839 of the chamber housing 824.

A mouthpiece 855 is located on the outside of the downstream portion 845. Formed in the interior of the mouthpiece is a sealing ledge 847. Exhalation ports 890 are disposed on the sides of the mouthpiece 855. The exhalation ports 890 are preferably generally rectangular shaped openings. Exhalation valves (not shown) could be built into the exhalation ports 890 in order to avoid the entrainment of any ambient air in the mouthpiece 855 before a valve 880 is opened.

As shown in FIGS. 23–25, a baffle retainer member 856 is located in the mouthpiece 855 near where the mouthpiece 855 intersects the downstream portion 843. The baffle retainer member 856 includes a containment baffle 851, a retainer 853 and connecting members 857. The retainer 853 includes an inner wall 862, an outer wall 864 and a rear wall 866. In a preferred embodiment, the baffle retainer member 856 is attached to the mouthpiece 855 by snap fit to the mouthpiece. Alternatively, the baffle retainer member 856 can be attached to the mouthpiece 855 using an adhesive or by ultrasonic welding.

Referring to FIG. 23, the containment baffle 851 is located centrally and is operatively attached with the retainer 853 by the connecting members 857. The containment baffle 851 is positioned to partially block the output end 848. As shown in FIG. 23, the containment baffle 851 is preferably dome shaped and has a concave surface and a convex surface. Like the embodiment shown in FIGS. 1–11, the containment baffle 851 is aligned with a central axis 842 of the housing 824 and is directly in line with a discharge orifice 836. The convex surface of the containment baffle faces downstream. The containment baffle 851 reduces the forward, on-axis velocity and simultaneously acts as an impaction surface for on-axis projectile aerosol medication particles.

As shown in FIG. 24–25, the inner wall 862, outer wall 864 and rear wall 866 of the retainer 853 join to form a channel 869. In addition, inhalation openings 870 are formed between the inner wall 862 and the outer perimeter of the containment baffle 851. The inhalation openings 870 are arcuate in shape and conform to the inner wall 862 and the outer perimeter of the containment baffle 851.

Referring to FIGS. 23–25 a valve 880 is disposed in the mouthpiece and includes a valve member 885 and a valve seat 887. The valve 880 is positioned so that it can block the inhalation openings 870. The valve 880 is designed to allow medication to be withdrawn through the mouthpiece but prevents backflow into the chamber housing.

In the embodiment shown, the valve member 885 has a central open area 881, an inner portion 882 having an outer portion 884. The inner portion 882 has a sealing portion 879 that is formed along the inner periphery of the inner portion 882. The sealing portion 879 forms a continuous surface. An engaging member 883 is located on the outer portion 884 and is designed to be movable within the channel 869. The valve member 885 and the central open area 881 are preferably circular shaped. Alternatively they may be square shaped, rectangular shaped, triangular shaped, trapezoidal shaped or elliptical shaped. The valve member 885 is preferably made of a rigid material such as plastic or metal. In a preferred embodiment, the valve member 885 is made of polypropylene or polyethylene. Alternatively, the valve member 885 could be made of a flexible material such as silicone, a thermoplastic elastomer, rubber or Ethylene-Propylene-Diene-Monomer (EPDM).

The valve seat 887 has a sealing surface 888 that is formed on the outer perimeter of the concave surface of the containment baffle. The sealing surface 888 is sized and shaped to meet with the sealing portion 887.

The operation of the present embodiment is similar to that of the embodiment shown in FIGS. 1–11. The patient presses down on the pMDI canister to cause a plume of medication to be discharged from the pMDI canister out of the mouthpiece of the actuator boot and into the interior space 839. The patient then inhales the aerosol from the interior space 839 via the mouthpiece 855 of the apparatus 810.

The act of inhalation causes the valve 880 to move to an open or first position shown in FIG. 24. When the patient inhales the valve member 885 moves downstream away from the valve seat 887 and a gap 892 is created between the sealing surface 888 and the sealing portion 879. In this first position, the outer portion 884 is positioned adjacent the sealing ledge 847. The engaging member 883 is located at the opening of the channel 869. In this first position, the valve 880 allows aerosol from the interior space to flow through the inhalation openings 870, through the gap, then through the central open area 881, then through the mouthpiece 855 to the patient. Also in this first position the engaging member 883 covers exhalation ports 890. Thus, during inhalation the valve member 885 moves downstream and blocks the exhalation ports 890.

The act of exhalation causes the valve 880 to move to a closed or second position shown in FIG. 25. In this second position, the inner portion 882 is located so that it preferably completely covers the inhalation openings 870 and the sealing portion 579 mates with the sealing surface 888 so that it is disposed adjacent the sealing surface 888. The engaging member 883 is substantially disposed within the channel 869. In this second position, the valve 880 prevents exhaled air and aerosol from flowing back into the chamber 824 and instead directs this exhaled air and aerosol to flow through the exhalation ports 890.

Still another embodiment of the aerosol medication delivery apparatus is shown in FIGS. 26–30. An aerosol delivery apparatus 910 includes a chamber housing 924 having an input end 946 and an output end 948 defining ends of an interior space 939. The chamber housing 924 is formed of a main housing portion 943 and a downstream portion 945 that together define the interior space 939 of the chamber housing 924. The apparatus 910 also includes an elastomeric backpiece 927 which may be similar to the backpieces 527, 627 in the embodiments shown in FIGS. 17 and 19. The output end of the chamber housing 924 is shaped to receive the downstream portion 945 and includes locking tabs 990 and a protrusion 971, the protrusion 971 is preferably annular in shape. The locking tabs 990 are spaced apart around the outside of the output end 948.

Figure 30:
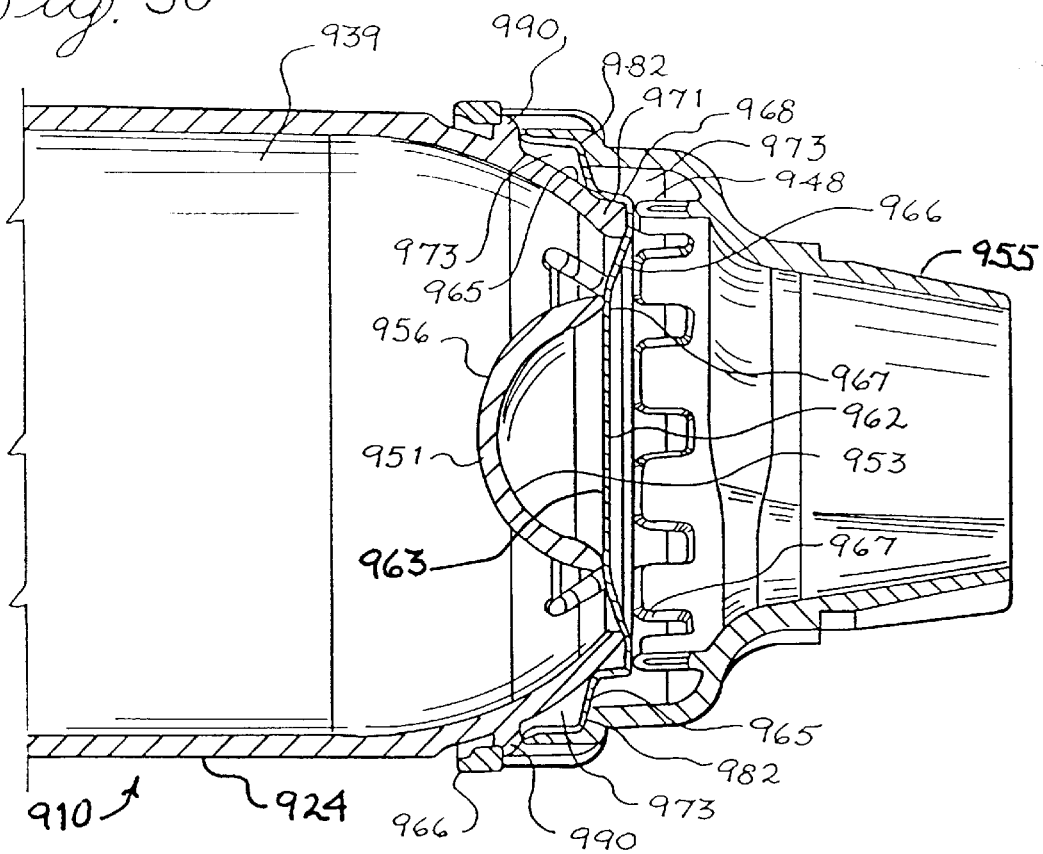
FIG. 30 is a side sectional view of the embodiment of FIG. 26.

Referring to FIGS. 26, 29 and 30 the downstream portion 943 includes a mouthpiece 955. The downstream portion 943 includes apertures 980, a sealing ledge 982, retaining ribs 984 and gaps 986 formed between the retaining ribs 984. The downstream portion 943 is connected to the output end 948 of the chamber housing 924 by placing the apertures 980 over the locking tabs 990. As shown in FIG. 29, the retaining ribs 984 are spaced apart from an inner surface 985 of the downstream portion 945. The sealing ledge 982 is preferably circular shaped.

In the embodiment of FIGS. 26–30, a containment baffle 951 may be formed of a single piece of material with the chamber housing 924, and located near the output end 948. As shown in FIG. 26, the containment baffle includes connecting members 969 that lead from the outer periphery of the containment baffle 951 to the inside of the chamber housing 924. Inhalation openings 970 are formed between the outer periphery of the containment baffle 951 and the chamber housing 924 and are separated by the connecting members 969. The inhalation openings 970 are arcuate in shape and conform to the outer perimeter of the containment baffle 951. In a preferred embodiment the containment baffle 951 is dome shaped and has a concave surface 953 and a convex surface 956. The convex surface 956 of the dome points towards the input end 946 of the chamber 924. Alternatively, the containment baffle 951 could be square shaped, rectangular shaped, elliptical shaped, circular shaped, trapezoidal shaped, triangular shaped or oblong shaped.

Referring to FIG. 26, a valve 960 having a valve member 962 and a valve seat 964 is shown. The valve seat 964 has a sealing surface 966 that is preferably formed on the outer perimeter of the downstream side of the containment baffle 951. In a preferred embodiment, the valve seat 964 conforms to the shape of the downstream portion of the containment baffle 951. In the embodiment shown, the valve seat 964 is generally circular in shape.

Referring again to FIG. 26, a valve member 962 includes a central open area 961, an inner portion 963, an outer portion 965 and an outer wall 968. The inner portion 963 is sized and shaped to cover the inhalation openings 970. As shown in FIG. 28, a sealing portion 967 is located toward the interior of the inner portion 963. Referring to FIG. 30, the sealing portion 967 is shaped to mate with the sealing surface 966. The sealing portion 967 forms a continuous surface. The outer wall 968 is shaped to mate with the protrusion 971.

In a preferred embodiment, the central open area 961, the inner portion 963 and the outer portion 965 are circular in shape. Alternatively, the inner portion 963, the outer portion 965 and the central open area 961 may be shaped differently, such as square shaped, rectangular shaped, elliptical shaped, circular shaped, trapezoidal shaped, triangular shaped or oblong shaped. The outer wall 968 is preferably shaped to conform with the protrusion 971. In the embodiment shown, the outer wall 968 is annular shaped. As shown in FIG. 28, the valve member 962 is partially dome shaped in cross section. The valve member 962 is preferably made of plastic such as silicone or from a thermoplastic elastomer. Alternatively, the valve may be made of rubber or EPDM.

The operation of the apparatus 910 will now be discussed with reference to FIGS. 30–32. Referring to FIG. 30, the apparatus 910 is shown as assembled prior to inhalation by the patient. At rest, the valve member 962 is adjacent with the output end 948 of the chamber housing 924. Referring to FIGS. 26, the inner portion 963 covers the inhalation openings 970. Referring again to FIGS. 30–32, the sealing portion 967 of the inner portion 963 of the valve member 962 mates with the sealing surface 966 of the containment baffle 951. The retaining ribs 984 of the mouthpiece 955 press the inner portion 963 against the output end 948 of the chamber housing 951 thereby generally holding the valve member 962 in place. The outer portion 965 is preferably located in a peripheral opening formed in between the sealing ledge 982 and the chamber housing 924.

The operation of this embodiment is similar to the operation of the embodiment of FIGS. 17 and 18; the patient presses down on the pMDI canister to cause a plume of aerosol medication to be discharged from the stem of the pMDI canister out of the mouthpiece of the actuator boot and into the interior space 939. The patient inhales the aerosol from the interior space 939 via the mouthpiece 955 of the apparatus 910.

Figure 31:
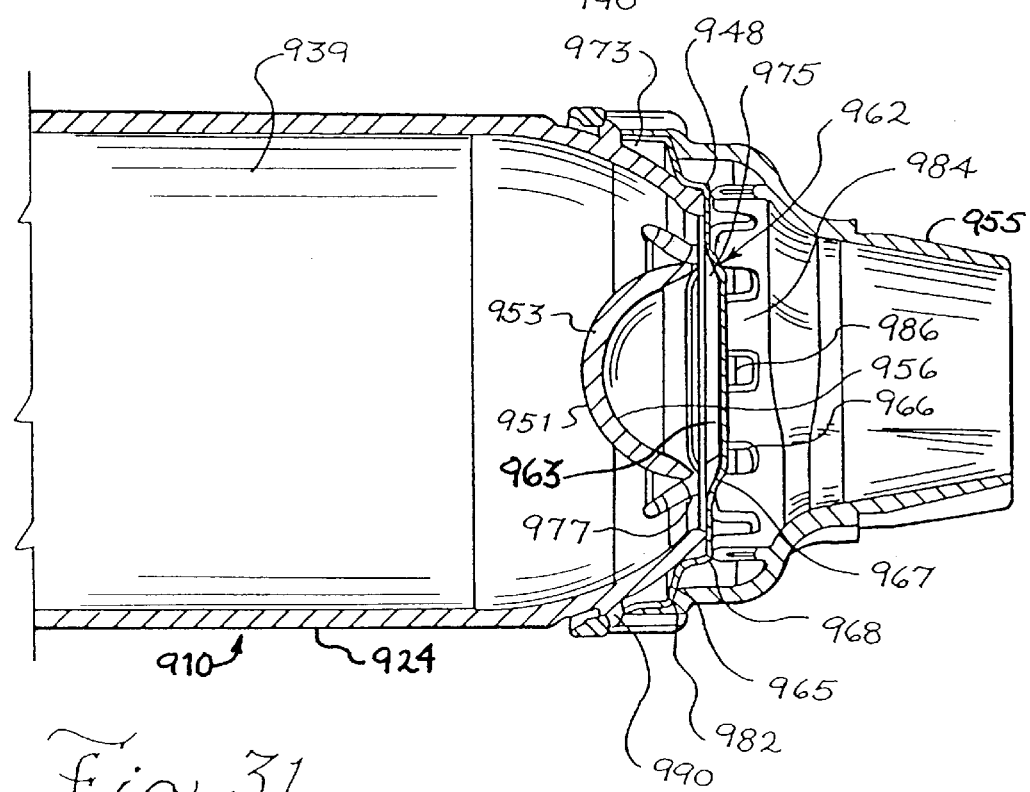
FIG. 31 is a side sectional view of the embodiment of FIG. 26 shown during inhalation by the patient.

Referring to FIG. 31, inhalation by the patient causes the sealing portion 967 to lift off of the sealing surface 966. This creates a gap 977 between the sealing portion 967 and the sealing surface 966. The gap 977 is uniform in size. The aerosol medication travels through the gap 977 and into the mouthpiece 955 where it may be inhaled by the patient.

Figure 32:
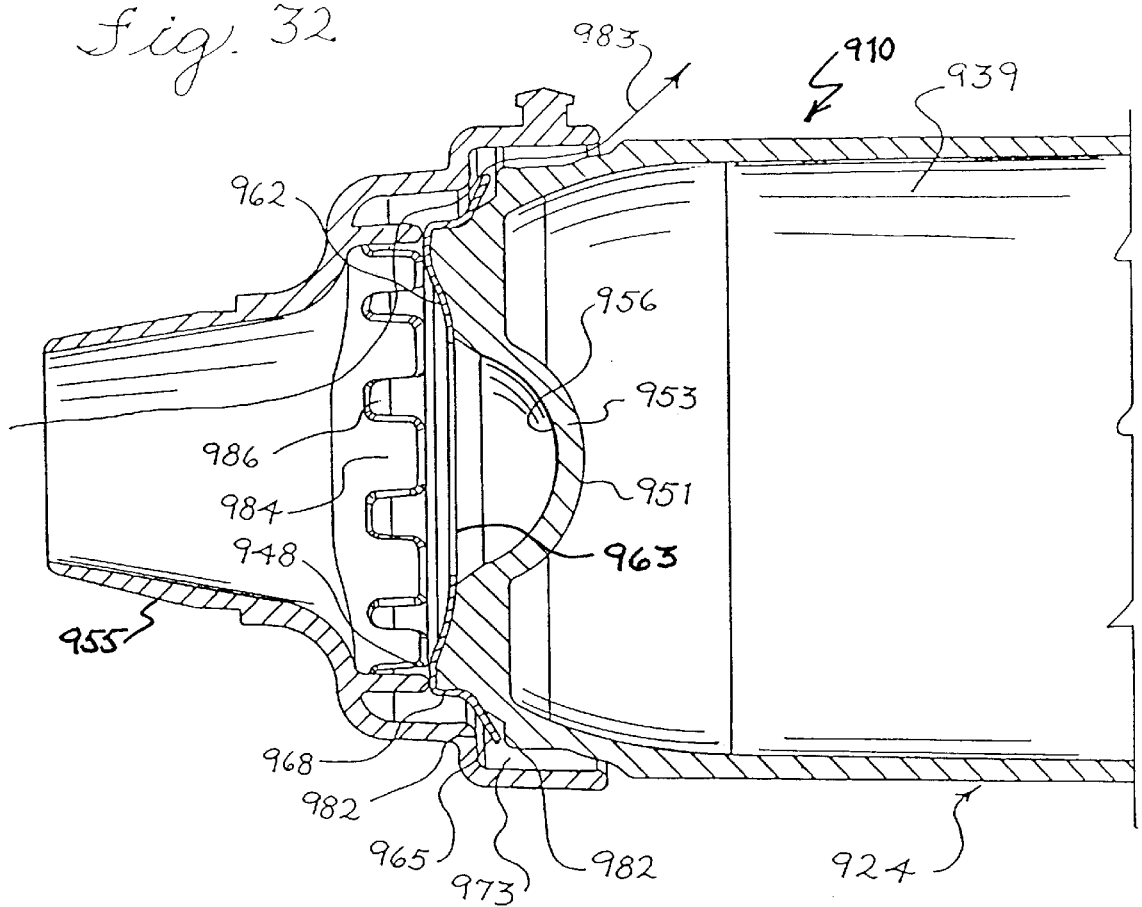
FIG. 32 is a side sectional view of the embodiment of FIG. 26 shown during exhalation by the patient.
Figure 35:
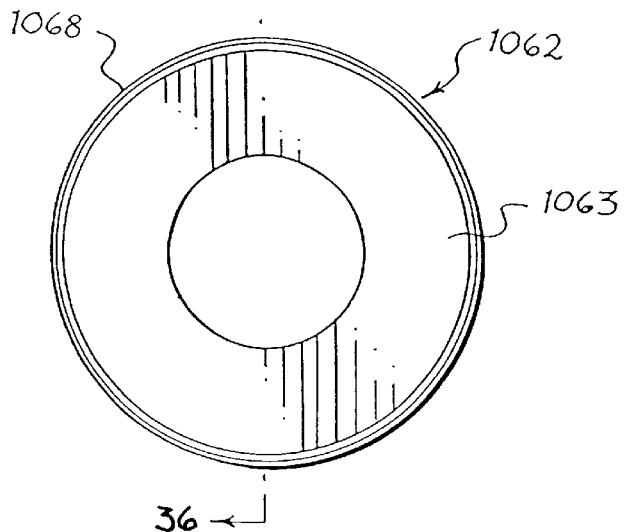
FIG. 35 is a front view of the valve used in the embodiment of FIG. 33.
Figure 36:
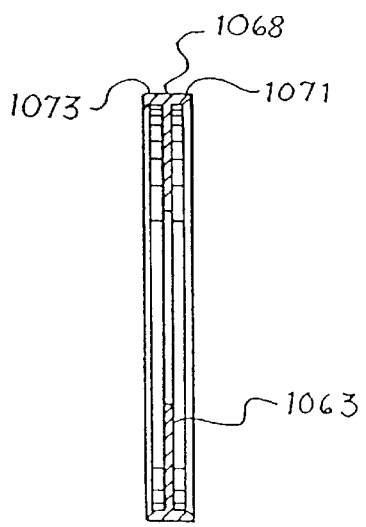
FIG. 36 is a side sectional view of the valve shown in FIG. 35.

Referring to FIG. 32, the patient may then exhale into the mouthpiece 955. Exhalation by the patient, results in air travelling through the mouthpiece 955. This air then passes through the openings in between the retaining ribs 984. Next the force of the exhaled air causes the outer portion 965 of the valve member 962 to move away from the annular sealing ledge 982 in a direction towards the chamber housing 924. As a result a passageway is created between the outer portion 965 and the annular sealing ledge 982 through which the exhaled air passes out to the atmosphere. An arrow 983 schematically illustrates a possible pathway of the exhaled air.

An advantageous feature of the embodiment disclosed in FIGS. 26–32 is provided by the partial domed cross sectional shape of the valve member 962. This shape provides for a secure seal between the sealing portion 967 and the sealing surface 966. The partial domed cross sectional shape of the inner portion 963 also causes the sealing portion 967 to spring back against the sealing surface after the completion of inhalation by the patient, thereby ensuring the integrity of the seal for the next use of the apparatus.

A further advantage is provided by the outer portion 965 moving against the sealing ledge 982 during inhalation. This prevents ambient air from leaking into the mouthpiece 955 during inhalation. As a result a lower flow rate of inhalation is required to open the valve to allow the aerosol medication to exit the chamber thereby making it easier for users that have low inhalation flow rates, such as young children and people of old age to open the valve so that they may inhale the medication.

Another embodiment of the aerosol medication delivery apparatus is shown in FIGS. 33–36. An aerosol delivery apparatus 1000 includes a chamber housing 1024 having an input end 1046 and an output end 1048. The apparatus also includes an elastomeric backpiece which may be similar to the backpiece in the embodiment shown in FIGS. 17 and 18. The chamber housing 1024 has a connecting portion 1025 formed near the output end 1048. A locking ridge 1056 is formed at the downstream end of the connecting portion 1025. The locking ridge 1056 is preferably annular in shape. In a preferred embodiment, the diameter of the chamber housing gradually increases from the input end 1046 to the output end 1048.

Referring to FIG. 33, the apparatus 1000 includes a baffle member 1050. The baffle member has a connecting edge 1053 that is generally sized and shaped to telescopically fit within the connecting portion 1025 to fix the baffle member 1050 to the chamber housing 1024.

The apparatus 1000 has a downstream portion 1045. The downstream portion 1045 includes a mouthpiece 1055. The inside of the downstream portion 1045 includes an inner surface 1085, a recessed portion 1087 and exhalation ports 1089. Connecting clips 1057 are spaced apart along the inside surface of the mouthpiece. The recessed portion 1087 is preferably annular shaped. The downstream portion 1045 is disposed around the baffle member 1050 and fixed to the baffle member 1050 by the connecting clips 1057 which lock onto the locking ridge 1056.

The baffle member 1050 includes a containment baffle 1051 at its downstream end. The containment baffle is similar to the containment baffle in the embodiment shown in FIGS. 26–32. A receiving member 1057 is formed at the downstream end of the baffle member 1050 and is positioned concentrically with respect to the containment baffle 1051. The receiving member 1057 is preferably annular in shape.

Referring again to FIG. 33, a valve 1060 is shown having a valve member 1062 and a valve seat 1064. The valve seat 1064 has a sealing surface 1066 that is preferably formed on the outer perimeter of the downstream side of the containment baffle 1051. In a preferred embodiment, the valve seat 1064 conforms to the shape of the downstream portion of the containment baffle 1051. In the embodiment shown, the valve seat 1064 is generally circular in shape.

As shown in FIGS. 33–36, the valve member 1062 includes a central open area 1061 an inner portion 1063, and an engaging member 1068. The engaging member 1068 has an input side 1071 and an output side 1073. The input side 1071 of the engaging member 1068 is concentrically positioned around the receiving member 1057. The output side 1073 of the engaging member 1068 is disposed within the recessed portion 1087. The inner portion 1063 is sized and shaped to cover inhalation openings 1070. As shown in FIG. 34, a sealing portion 1067 is located near the interior of the inner portion 1063. Referring to FIG. 34, the sealing portion 1067 is shaped to mate with the sealing surface 1066. The sealing portion 1067 forms a continuous surface.

In a preferred embodiment, the central open area 1061 and the inner portion 1063 are circular in shape. Alternatively, they may be square shaped, rectangular shaped, elliptical shaped, circular shaped, trapezoidal shaped, triangular shaped or oblong shaped. In the embodiment shown, the engaging member 1068 is annular shaped. The valve member 1062 is preferably made of plastic such as silicone or from a thermoplastic elastomer. Alternatively, the valve member 1062 may be made of rubber or EPDM.

The operation of the present embodiment is generally the same as the embodiment shown in FIGS. 26–32. The primary difference is that when the patient exhales, the majority of the exhaled air exits through the exhalation ports 1089 formed on the downstream portion 1045.

Still another embodiment of the aerosol medication delivery apparatus is shown in FIGS. 37 and 38. In FIG. 37, an aerosol medication delivery apparatus 1110 includes components that are similar to the previous embodiments, in particular the embodiments shown in FIGS. 26–32 and FIGS. 33–36. A chamber housing 1124 having an input end 1146 and an output end 1148 defines an interior space 1139. The chamber housing also includes locking tabs 1190.

Instead of a mouthpiece, however, the downstream portion of the chamber housing 1124 has a mask 1155 that may be positioned over the patient's mouth and against part of a patient's face. Referring to FIG. 37, the mask 1155 includes a gripping ring 1151 located inside the mask at the upstream end, a frustoconical section 1153 that is formed with the gripping ring 1151 and extends downstream, and an end portion 1154 that is located downstream of and formed with the frustoconical section 1153. The end portion 1154 is preferably circular in shape. A housing 1157 is formed on the top portion of the mask and an exhalation valve 1159 is formed in this housing 1157. The mask 1155 may be similar to the mask described in U.S. Pat. No. 5,645,049 or in Ser. No. 08/842,956, the entire disclosures of which are incorporated by reference herein.

Referring to FIGS. 37 and 38 the apparatus includes an attachment member 1140. The attachment member 1140 includes a connecting portion 1142 that includes apertures 1144. The connecting portion 1142 is generally sized and shaped to be disposed over the output end 1148 of the chamber housing 1124. The attachment member 1140 is fixed to the chamber housing 1124 by placing the apertures 1144 over the locking tabs 1190. The attachment member 1140 has a mask retaining portion 1143 formed integral with and downstream of the connecting portion 1142. The mask retaining portion 1143 includes locking members 1146 that are spaced apart and protrude outward from the mask retaining portion 1143. The mask retaining portion 1143 is inserted within the mask 1155 so that the gripping ring 1151 cooperates with the locking members 1146 to securely fix the mask 1155 to the mask retaining portion 1143. A locking ring 1148 is formed in the inside of the mask retaining portion 1143. A sealing ledge 1147 is formed at the intersection of the connecting portion 1142 and the mask retaining portion 1143. The connecting portion 1142 and the mask retaining portion 1143 are preferably annular shaped. The sealing ledge 1147 and the locking ring 1148 are preferably circular shaped. Referring to FIG. 37, as assembled, the attachment member 1140 is fixed to the chamber housing 1124 by disposing the apertures 1144 over the locking tabs 1190.

A valve 1160, including a valve seat 1162 and a valve member 1164, similar to the valve 1160 in the embodiment shown in FIGS. 26–32 is disposed between the attachment member 1140 and the chamber housing 1124. A containment baffle 1151 similar to the containment baffle 1151 in the embodiment shown in FIGS. 26–32 is formed at the output end 1148 of the chamber housing 1124.

Referring again to FIG. 37, the locking ring 1148 presses an inner portion 1166 of the valve against connecting members formed on the containment baffle 1151.

The embodiment of FIGS. 37 and 38 may be used in a similar manner as the embodiment of FIGS. 26–32. One difference is that during exhalation, the exhaled air passes out to the atmosphere through the exhalation valve.

Figure 40:
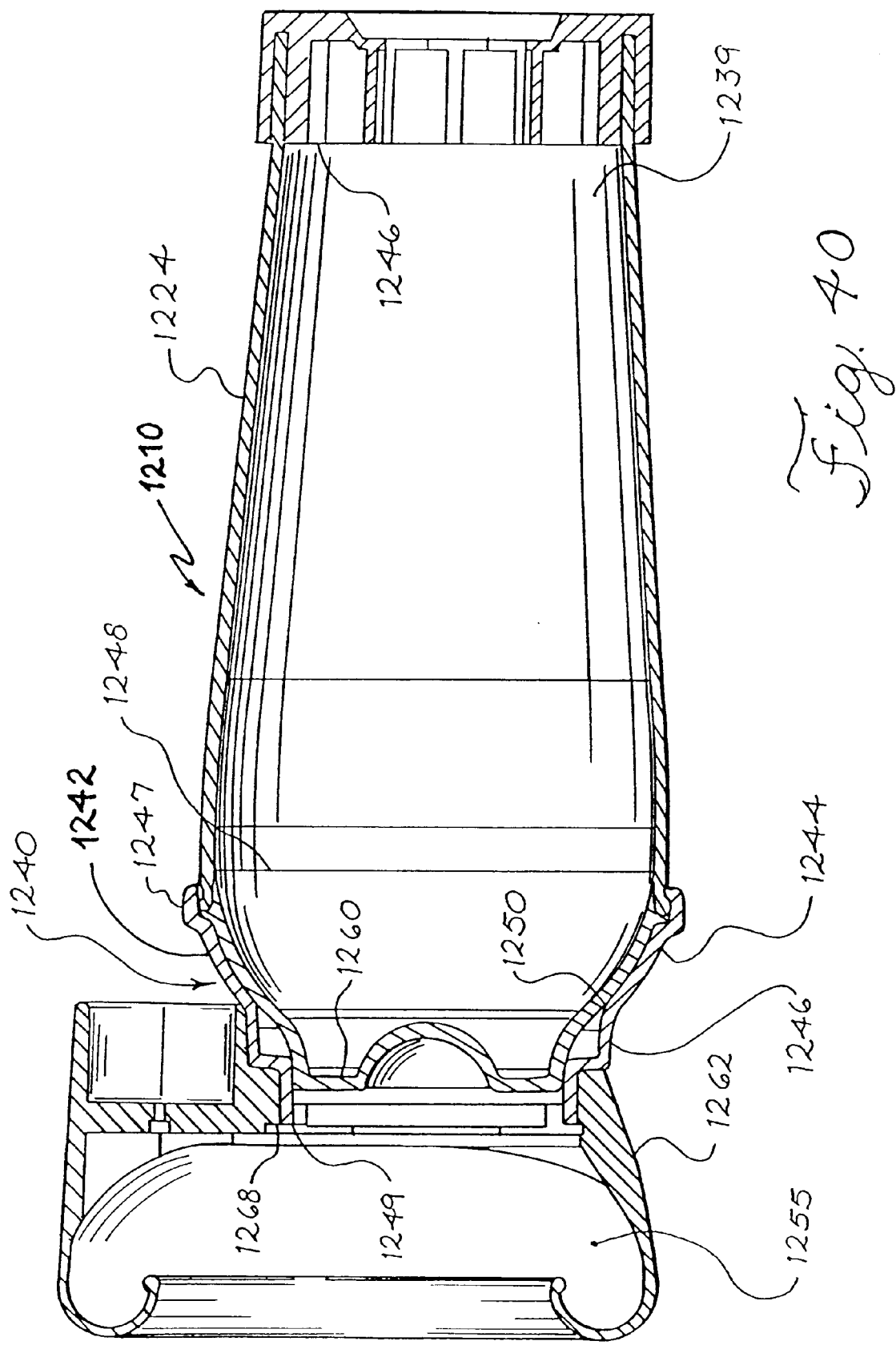
FIG. 40 is a side sectional view of the embodiment of FIG. 39.

Still another embodiment of the aerosol medication delivery apparatus is shown in FIGS. 39 and 40. In FIGS. 39 and 40, the aerosol delivery apparatus 1210 includes components that are similar to the previous embodiments, in particular to the embodiment of FIGS. 33–36 and 37–38. The chamber housing 1224 includes an input end 1246 and an output end 1248 that define the interior space 1239.

This embodiment includes a baffle member 1250, a valve 1260 and a mask 1255. The baffle member 1250 is similar to the baffle member shown in FIGS. 33–34. The mask 1255 is similar to the mask shown in FIG. 37. The valve 1260 is similar to the valve shown in FIGS. 33–36 and has a valve member 1262 that includes an engaging member 1268 having an inside side and an outside side. The apparatus also includes an attachment member 1240 similar to the attachment member in the embodiment shown in FIGS. 39 and 40. In this case, a connecting portion 1242 of the attachment member 1240 is sized and shaped to be disposable over the baffle member 1250. The connecting portion 1242 includes a first portion 1244 having a locking ring 1247 and a second annular portion 1246 formed downstream of the first portion 1244. A mask retaining portion 1243 of the connecting portion 1242 is located downstream of and formed with the annular portion 1244. The mask retaining portion 1243 is similar to the mask retaining portion of the embodiment shown in FIGS. 38 and 39. The mask retaining portion 1243 includes a recess 1249 that is preferably sized and shaped to receive the valve member 1262.

Referring to FIG. 40, the outside side of the valve member 1262 is disposed in the recess, where as the inside side of the valve member 1262 is concentrically positioned adjacent a receiving member 1257 formed on a downstream portion of the baffle member 1250.

The embodiment of FIGS. 39 and 40 may be used in a similar manner as the embodiment of FIGS. 37 and 38.

Referring to FIG. 41, an alternative embodiment of a valve member 1362 for use with the present invention is shown. The valve member 1362 is similar to the valve member in the embodiment shown in FIGS. 26–32. The primary difference is that the valve member 1362 has a central opening 1361 that is substantially smaller sized diameter.

Referring to FIG. 42, an alternative embodiment of a valve member 1462 for use with the present invention is shown. The valve member 1462 is similar to the valve member in the embodiment shown in FIGS. 26–32. The primary difference is that the valve member 1462 includes a center member 1463 disposed in the middle of the central open area 1461. In the embodiment shown, the center member 1463 is cross shaped.

Referring to FIG. 43, an alternative embodiment of a downstream portion 1545 for use with the present invention is shown. The downstream portion 1545 is similar to the downstream portion in the embodiment shown in FIGS. 26–32. The primary difference is that a mouthpiece 1555 on the downstream portion 1545 is circular in shape and designed to be used in conjunction with an endotracheal tube or other similar tube.

An advantageous feature of the embodiments disclosed in FIGS. 23–40 is provided by the valve member. The valve member tends to provide a more uniform flow than prior art valve members because the sealing portion which provides the gap upon inhalation is a continuous surface. Further, because the deflection of the valve member from the output end is minimal as compared to prior art devices, less dead space is required between the valve member and the end of the mouthpiece.

The invention may be embodied in other forms than those specifically disclosed herein without departing from its spirit or essential characteristics. The described embodiments are to be considered in all respects only as illustrative and not restrictive, and the scope of the invention is commensurate with the appended claims rather than the foregoing descriptions.

We claim:

1. An aerosol medication delivery apparatus for use with a pressurized metered-dose inhaler canister having medication and a propellant contained therein under pressure, wherein the pressurized metered-dose inhaler canister has a discharge orifice from which the medication and propellant can be discharged forming an aerosol, the apparatus comprising:

a chamber housing having an input end and an output end and defining an interior space;

a containment baffle located at the output end, wherein the containment baffle includes a convex surface; and a valve located at the output end comprising a valve seat formed on the containment baffle and a valve member, the valve seat having a sealing surface formed on an outer perimeter of the containment baffle, and the valve member having a central open area and a sealing portion at a perimeter of the central open area that mates with the sealing surface.

2. The aerosol medication delivery apparatus of claim 1, wherein the convex surface faces downstream away from the input end of the chamber.

3. The aerosol medication delivery apparatus of claim 1, further comprising a retainer defining a channel, the retainer located near the output end.

4. The aerosol medication delivery apparatus of claim 3, further comprising an engaging member located on the valve member, wherein the engaging member is movable between a first position and a second position within the channel.

5. The aerosol medication delivery apparatus of claim 1, wherein the convex surface faces toward the input end of the chamber housing.

6. The aerosol medication delivery apparatus of claim 1, wherein the central open area is circular shaped.

7. The aerosol medication delivery apparatus of claim 1, wherein the valve member has an inner portion, an outer portion and an engaging member.

8. The aerosol medication delivery apparatus of claim 7, wherein at least one inhalation opening is located near the output end and are defined between the containment baffle and the chamber housing.

9. The aerosol medication delivery apparatus of claim 8 wherein the inner portion is positioned adjacent the at least one inhalation opening.

10. The aerosol medication delivery apparatus of claim 8, further comprising a protrusion formed near the output end on an outer surface of the chamber housing.

11. The aerosol medication delivery apparatus of claim 10, wherein the engagement member concentrically surrounds the protrusion.

12. The aerosol delivery apparatus of claim 1, wherein the valve member is dome shaped in cross section.

13. The aerosol delivery apparatus of claim 1, further comprising a downstream portion attached with the output end.

14. The aerosol medication delivery apparatus of claim 13, wherein the downstream portion has an inner surface and a plurality of retaining ribs spaced apart from the inner surface.

15. The aerosol medication delivery apparatus of claim 14, wherein the retaining ribs define gaps which permit exhaled air to flow through to the atmosphere.

16. The aerosol delivery apparatus of claim 1, wherein the valve member is made of a rigid material.

17. The aerosol delivery apparatus of claim 1, wherein the sealing portion forms a continuous surface.

18. The aerosol medication delivery apparatus of claim 1 wherein said baffle further comprises a concave surface.

19. The aerosol medication delivery apparatus of claim 1 wherein said baffle further comprises a concave surface opposite said convex surface.

20. The aerosol medication delivery apparatus of claim 1 wherein said central open area is formed in the same plane as said sealing portion.

21. The aerosol medication delivery apparatus of claim 1, wherein said containment baffle comprises a center baffle portion having said convex surface.

22. The aerosol medication delivery apparatus of claim 21, wherein said containment baffle further comprises at least one connecting member extending radially outward from said center baffle portion.

23. The aerosol medication delivery apparatus of claim 22, wherein said containment baffle further comprises an outer receiving portion positioned concentrically around said baffle portion, wherein said at least one connecting member extends radially between said receiving portion and said baffle portion.

24. The aerosol medication delivery apparatus of claim 23, wherein said valve seat comprises a first valve seat formed on said baffle portion and second valve seat formed on said receiving portion, and wherein said sealing surface comprises a first sealing surface defined by said first valve seat formed on said baffle portion and a second sealing surface defined by said second valve seat formed on said receiving portion, and wherein said sealing portion of said valve member comprises a first sealing portion mating with said first sealing surface and a second sealing portion mating with said second sealing surface.

25. The aerosol medication delivery apparatus of claim 23, wherein said valve seat and said sealing surface thereof are formed on said receiving portion.

26. The aerosol medication delivery apparatus of claim 23, wherein said valve seat and said sealing surface thereof are formed on said baffle portion.

27. An aerosol medication delivery apparatus for use with a pressurized metered-dose inhaler canister having medication and a propellant contained therein under pressure, wherein the pressurized metered-dose inhaler canister has a discharge orifice from which the medication and propellant can be discharged forming an aerosol, the apparatus comprising:

a chamber housing having an input end and an output end and defining an interior;

a containment baffle located at the output end, wherein the containment baffle is dome shaped and includes a concave surface and a convex surface, wherein the convex surface faces toward the input end of the chamber housing; and a valve located at the output end comprising a valve seat and a valve member, the valve seat having a sealing surface, and the valve member having a central open area and a sealing portion at a perimeter of the central open area that mates with the sealing surface.

* * * * *